United States Patent
Lee et al.

(10) Patent No.: US 11,745,179 B2
(45) Date of Patent: Sep. 5, 2023

(54) MICROFLUIDIC SYSTEMS AND METHODS FOR LIPOPLEX-MEDIATED CELL TRANSFECTION

(71) Applicants: THE REGENTS OF THE UNIVERSITY OF CALIFORNIA, Oakland, CA (US); PIONEER HI-BRED INTERNATIONAL, INC., Johnston, IA (US)

(72) Inventors: Abraham P. Lee, Irvine, CA (US); Xuan Li, Irvine, CA (US); Yue Yun, Johnston, IA (US)

(73) Assignees: THE REGENTS OF THE UNIVERSITY OF CALIFORNIA, Oakland, CA (US); PIONEER HI-BRED INTERNATIONAL, INC., Johnston, IA (US)

( * ) Notice: Subject to any disclaimer, the term of this patent is extended or adjusted under 35 U.S.C. 154(b) by 255 days.

(21) Appl. No.: 16/756,820

(22) PCT Filed: Oct. 22, 2018

(86) PCT No.: PCT/US2018/056852
§ 371 (c)(1),
(2) Date: Apr. 16, 2020

(87) PCT Pub. No.: WO2019/079787
PCT Pub. Date: Apr. 25, 2019

(65) Prior Publication Data
US 2020/0324288 A1 Oct. 15, 2020

Related U.S. Application Data

(60) Provisional application No. 62/671,859, filed on May 15, 2018, provisional application No. 62/575,201, filed on Oct. 20, 2017.

(51) Int. Cl.
*B01L 3/00* (2006.01)
*C12M 1/00* (2006.01)
*C12M 3/06* (2006.01)

(52) U.S. Cl.
CPC ... *B01L 3/502715* (2013.01); *B01L 3/502769* (2013.01); *C12M 21/00* (2013.01); *C12M 23/16* (2013.01); *B01L 2300/0877* (2013.01)

(58) Field of Classification Search
CPC .. B01L 3/502715; B01L 3/5027; B01L 3/502; B01L 3/50; B01L 3/502769;
(Continued)

(56) References Cited

U.S. PATENT DOCUMENTS 2,656,508 A 10/1953 Coulter
3,380,584 A 4/1968 Fulwyler
(Continued)

FOREIGN PATENT DOCUMENTS

GB 2395196 5/2004
WO WO2007120240 A2 10/2007
(Continued)

OTHER PUBLICATIONS

Loizou, Inventions 2018, 3(3), 54; https://doi.org/10.3390/inventions3030054. (Year: 2018).*
(Continued)

*Primary Examiner* — Christine T Mui
(74) *Attorney, Agent, or Firm* — NGUYEN TARBET LLC

(57) ABSTRACT

Systems and methods for transfection using a microfluidic device are disclosed. Microdroplets encapsulate cells, transfection molecules, and cationic lipid transfection reagent. Droplet chaotic advection in a rendering channel of the system results in a uniform lipid-DNA complex (lipoplex) formation, which can improve gene delivery efficacy. The
(Continued)

shear stress exerted on cell membranes during the chaotic mixing increases membrane permeability, which when combined with the co-confinement of cell and lipoplex, improves transfection efficiency of the cell. The systems and methods can be used for a variety of applications such as gene therapy, in vitro fertilization, regenerative medicine, cancer treatment, and vaccines.

18 Claims, 8 Drawing Sheets

Specification includes a Sequence Listing.

(58) Field of Classification Search
CPC ..... B01L 2300/0877; B01L 2300/0861; B01L 2300/08; C12M 21/00; C12M 23/16; C12M 23/02; C12M 23/00
USPC ................................................. 422/504, 500
See application file for complete search history.

(56) References Cited

U.S. PATENT DOCUMENTS

| | | | |
|---|---|---|---|
| 4,009,435 A | 2/1977 | Hogg | |
| 5,465,582 A | 11/1995 | Bliss et al. | |
| 8,263,023 B2 | 9/2012 | Le Vot et al. | |
| 8,365,311 B2 | 1/2013 | Nawarathna | |
| 8,927,040 B2 | 1/2015 | Brand et al. | |
| 9,176,504 B2 | 11/2015 | Chiou et al. | |
| 2002/0182654 A1 | 12/2002 | Jing et al. | |
| 2004/0068019 A1* | 4/2004 | Higuchi ............. | B01F 33/3011 |
| | | | 516/9 |
| 2004/0234588 A1 | 11/2004 | Lu et al. | |
| 2005/0015001 A1 | 1/2005 | Lec et al. | |
| 2005/0106064 A1 | 5/2005 | Laurell et al. | |
| 2005/0272039 A1 | 12/2005 | Yasuda | |
| 2005/0272096 A1 | 12/2005 | Clague et al. | |
| 2006/0051329 A1 | 3/2006 | Lee et al. | |
| 2006/0177815 A1 | 8/2006 | Soh et al. | |
| 2007/0264320 A1 | 11/2007 | Lee et al. | |
| 2008/0038807 A1 | 2/2008 | Pommersheim | |
| 2008/0241875 A1 | 10/2008 | Hwang et al. | |
| 2009/0042310 A1 | 2/2009 | Ward et al. | |
| 2009/0068170 A1 | 3/2009 | Weitz et al. | |
| 2009/0075390 A1 | 3/2009 | Linder et al. | |
| 2009/0286300 A1 | 11/2009 | Le Vot et al. | |
| 2009/0298191 A1 | 12/2009 | Whitesides et al. | |
| 2011/0059556 A1 | 3/2011 | Strey et al. | |
| 2011/0086352 A1 | 4/2011 | Bashir et al. | |
| 2011/0285042 A1 | 11/2011 | Viovy et al. | |
| 2012/0034155 A1 | 2/2012 | Hyde et al. | |
| 2012/0107912 A1 | 5/2012 | Hwang et al. | |
| 2012/0196288 A1 | 8/2012 | Beer | |
| 2013/0078163 A1 | 3/2013 | Chung et al. | |
| 2013/0154671 A1 | 6/2013 | Lee et al. | |
| 2013/0171628 A1 | 7/2013 | Di Carlo et al. | |
| 2013/0210649 A1 | 8/2013 | McKnight et al. | |
| 2014/0011291 A1 | 1/2014 | Patel et al. | |
| 2014/0068797 A1* | 3/2014 | Doudna ............... | C12N 15/902 |
| | | | 435/375 |
| 2014/0076430 A1 | 3/2014 | Miller et al. | |
| 2015/0018226 A1 | 1/2015 | Hansen et al. | |
| 2016/0033378 A1 | 2/2016 | Husain et al. | |
| 2016/0123858 A1 | 5/2016 | Kapur et al. | |
| 2016/0202153 A1 | 7/2016 | Gadini et al. | |
| 2017/0014449 A1 | 1/2017 | Bangera et al. | |
| 2017/0128940 A1 | 5/2017 | Amini et al. | |
| 2017/0145169 A1 | 5/2017 | Oakey et al. | |
| 2017/0165669 A1* | 6/2017 | Hung .................. | B01J 19/0093 |
| 2017/0183722 A1 | 6/2017 | Link | |
| 2018/0030515 A1 | 2/2018 | Regev et al. | |
| 2018/0078940 A1 | 3/2018 | Lee et al. | |

FOREIGN PATENT DOCUMENTS

| | | | |
|---|---|---|---|
| WO | WO2015157567 A1 | 10/2015 | |
| WO | WO2016040476 A1 | 3/2016 | |
| WO | WO2016126871 A2 | 8/2016 | |
| WO | WO2017070169 A1 | 4/2017 | |

OTHER PUBLICATIONS

International Search Report for PCT Application No. PCT/US18/56852 dated Jan. 11, 2019.
Lin, R., et al. "High efficiency cell encapsulation utilizing novel on-demand droplet generation scheme and impedance-based detection." 14th international conference on miniaturized systems for chemistry and life sciences, ed. H. Andersson-Svahn, S. Verpoorte, J. Emineus, N. Pam me. 2010.
J. Kim, M. Chung, S. Kim, D. H. Jo, J. H. Kim, and N. L. Jeon, "Engineering of a Biomimetic Pericyte-Covered 3D Microvascular Network," Plos One, vol. 10, p. e0133880, 2015.
X. Wang, D. T. T. Phan, A. Sobrino, S. C. George, C. C. W. Hughes, and A. P. Lee, "Engineering anastomosis between living capillary networks and endothelial cell-lined microfluidic channels," Lab on a Chip, vol. 16, pp. 282-290, 2016.
Mazutis, L. et al., Lab on a Chip, vol. 9, pp. 2665-2672 (2009).
Simon, M.G. et al., Label-Free Detection of DNA Amplification in Dropletsusing Electrical Impedance, 15th International Conference on Miniaturized Systems for Chemistry and Life Sciences 2011 (MicroTAS 2011), pp. 1683-1685 (Year: 2011).
Marsh et al. Room temperature ionic liquids and their mixtures—a review. Fluid Phase Equilibria 219 (2004) 93-98.
Oh, Woon Su, "Synthesis and applications of imidazolium-based ionic liquids and their polymer derivatives" (2012). Doctoral Dissertations. 1958. http://scholarsmine.mst.edu/doctoral_dissertations/1958.
Baret et al, "Fluorescence-activated droplet sorting (FADS): efficient microfluidic cell sorting based on enzymatic activity," Lab Chip. Jul. 7, 2009; 9(13):1850-8. doi: 10.1039/b902504a. Epub Apr. 23, 2009.
Macosko et al., "Highly Parallel Genome-wide Expression Profiling of Individual Cells Using Nanoliter, Droplets," Cell, vol. 161, No. 5, pp. 1202-1214, May 2015.
International Search Report for PCT Application No. PCT/US18/36962 dated Aug. 30, 2018.
International Search Report for PCT Application No. PCT/US18/36952 dated Sep. 18, 2018.
Kamalakshakurup et al. High-efficiency single cell encapsulation and size selective capture of cells in picoliter droplets based on hydrodynamic micro-vortices. Lab Chip, 2017, 17, 4324-4333.
Brouzes, Eric, et al. "Droplet microfluidic technology for single-cell high-throughput screening." Proceedings of the National Academy of Sciences106.34 (2009): 14195-14200.
S. I. Rubinow and J. B. Keller, "The transverse force on a spinning sphere moving in a viscous fluid," J. Fluid Mech., vol. 11, No. 03, p. 447, Nov. 1961.
Murata et al., Electrochemical single-cell gene-expression assay combining dielectrophoretic manipulation with secreted alkaline phosphatase reporter system, 2009, Biosensors and Bioelectronics, 25, 913-919.
Stinson et al., Genes Expressed in the Male Gametophyte of Flowering Plants and Their Isolation, 1987, Plant Physiol., 83, 442-447.
International Search Report for PCT Application No. PCT/US2016/056683 dated Dec. 27, 2016.
International Search Report for PCT Application No. PCT/US18/55722 dated Feb. 6, 2019.
International Search Report for PCT Application No. PCT/US17/55984 dated Dec. 14, 2017.
Doria, Arlene et al., "Rapid blood plasma separation with air-liquid cavity acoustic transducers", 15th International conference on miniaturized systems for chemistry and life sciences, Oct. 2-6, 2011, pp. 1882-1884.

(56) References Cited

OTHER PUBLICATIONS

Lee, Abraham P. et al., "Microfluidic air-liquid cavity acoustic transducers for on-chip integration of sample preparation and sample detection", Journal of laboratory automation, Dec. 2010, vol. 15, No. 6, pp. 449-454.
International Search Report Issued for PCT Application No. PCT/US2013/042735 dated Nov. 28, 2013.
Kobel, Stefan et al. "Optimization of microfluidic single cell trapping for long-term on-chip culture" Lab Chip, Dec. 2009, 857-863, Royal Society of Chemistry.

* cited by examiner

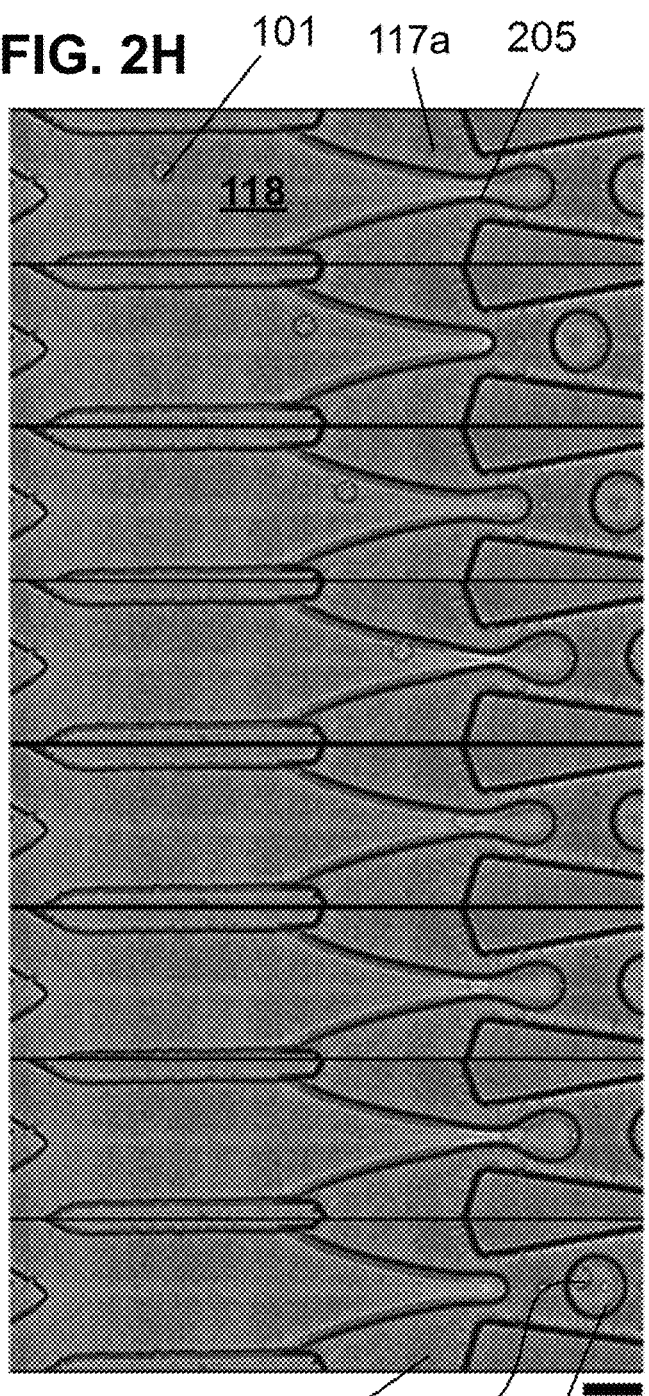
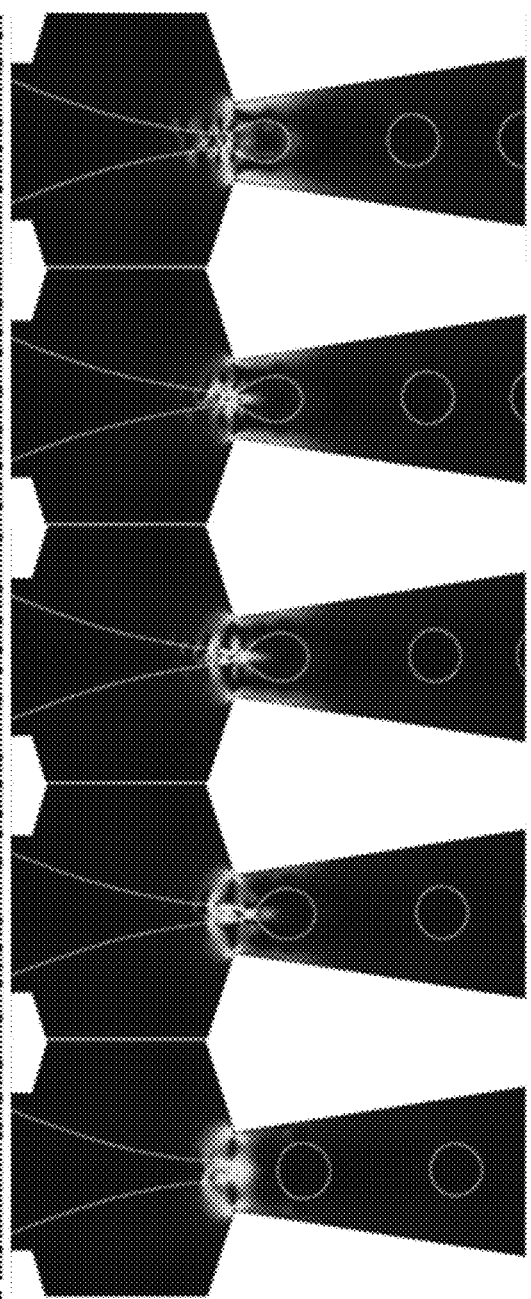
FIG. 2H
FIG. 2I
1.24×10⁻⁴     5.14×10²
Shear Stress (dyne/cm²)

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: sgTP53BP1 sequence

<400> SEQUENCE: 1
cagaatcatc ctctagaacc                                          20

<210> SEQ ID NO 2
<211> LENGTH: 3
<212> TYPE: DNA
<213> ORGANISM: Artificial Sequence
<220> FEATURE:
<223> OTHER INFORMATION: PAM sequence

<400> SEQUENCE: 2 tgg                                                             3

<210> SEQ ID NO 3
<211> LENGTH: 20
<212> TYPE: DNA
<213> ORGANISM: Artificial Sequence
<220> FEATURE:
<223> OTHER INFORMATION: forward primer sequence

<400> SEQUENCE: 3
ggttctagag gatgattctg                                          20

<210> SEQ ID NO 4
<211> LENGTH: 18
<212> TYPE: DNA
<213> ORGANISM: Artificial Sequence
```

-continued

```
<220> FEATURE:
<223> OTHER INFORMATION: reverse primer sequence

<400> SEQUENCE: 4
ttcaggattg gacacaac                                                         18
```

MICROFLUIDIC SYSTEMS AND METHODS FOR LIPOPLEX-MEDIATED CELL TRANSFECTION

CROSS REFERENCE

This application claims priority to U.S. Provisional Application No. 62/575,201 filed Oct. 20, 2017 and U.S. Provisional Application No. 62/671,859 filed May 15, 2018, the specification(s) of which is/are incorporated herein in their entirety by reference.

GOVERNMENT SUPPORT

This invention was made with Government support under Grant No. IIP-538813, awarded by the National Science Foundation. The Government has certain rights in this invention.

FIELD OF THE INVENTION

The present invention relates to transfection of cells, more particularly, to lipoplex-mediated transfection (lipofection) of single cells in a microfluidic device.

REFERENCE TO SEQUENCE LISTING

Applicant asserts that the information recorded in the form of an Annex C/ST.25 text file submitted under Rule 13ter.1(a), entitled UCI_17_23_PCT_Sequence List_ST25, is identical to that forming part of the international application as filed. The content of the sequence listing is incorporated herein by reference in its entirety.

BACKGROUND OF THE INVENTION

Transfection, which is the delivery of genetic materials into living cells, is challenging yet critical for many medical and biological applications including gene therapy, DNA vaccines, in vitro fertilization, cancer treatment, regenerative medicine, and induced pluripotent stem cells (IPSc), and plant cell gene editing. Numerous methods, such as viral vectors, non-viral vectors (e.g., cationic lipids, cationic polymers), electroporation, and micro-injection have been developed. However, current gene transfection methods (bench top approaches) typically require complicated procedures, have a low transfection efficiency/accuracy, and/or damage cell viability. For example, viral vectors have high transfection efficiency but can cause side effects like undesired mutation and immunogenicity. Electroporation provides higher transfection efficiency as compared to other non-viral methods, but uses high voltage pulses (kV levels) to generate transient pores in cell membranes so as to enable foreign molecules to enter the cell. On the other hand, non-viral vectors, such as cationic lipids, self-assemble with negatively charged nucleic acids into nanoparticles called lipoplexes (cationic lipid-nucleic acid complexes) by electrostatic interaction, and mediate gene transfection via endocytosis. While lipoplex-mediated intracellular delivery has been widely adopted in mammalian cell transfection, its lipoplex-mediated DNA transfection efficiency for suspension cells, e.g., lymphatic and hematopoietic cells, has been reported only at ~5% or lower. The lipoplex internalization is also inhibited by the sulphated proteoglycans on the cell membrane of hematopoietic cells.

In addition to a target cell's endocytic capability, another major determinant of lipofection efficiency is the size of the lipoplexes. Conventional bulk lipoplex preparation processes by hand shaking or vortexing yield a large size distribution of lipoplexes due to lack of control of the many variables, which adversely affects the lipofection efficiency and consistency since a significant fraction of the lipoplexes are either too large or too small for intracellular delivery. Furthermore, since the lipoplexes are typically used at low concentrations (1 μg/100 μL) to minimize cytotoxicity, the diffusion limitation in the bulk volume hinders lipoplex-cell interaction, which also limits the transfection efficiency.

Contrary to the bulk process, droplet microfluidics isolates reagents in monodispersed, picoliter liquid capsules and manipulates them at a throughput of thousands of droplets per second. Upon co-confinement in picoliter micro-reactors, the high surface-area-to-volume ratio and shorter diffusion distance at the microscale facilitate high reaction efficiency. Droplet microfluidics has also emerged as an effective tool for single-cell analysis, as it provides an isolated compartment for the single cell and its surrounding environment, thereby enabling quantitative control of the reagents due to monodispersity, and allowing for efficient and high throughput processing of tens of thousands of single cells.

Gene therapy is rapidly gaining momentum as a revolutionizing modality for the treatment of cancer, infectious diseases, and hereditary disorders. However, a key limitation in gene therapy development is the lack of efficient, safe, and controllable methods for intracellular delivery of exogenous materials to the cells. As such, gene therapy can significantly benefit from the advantages provided by droplet microfluidics. For instance, gene editing techniques, which involve addition, removal, or alteration of particular locations in the genome, utilize nucleic acids that do not easily cross into the cells; but by using droplet microfluidics, this can allow for the genetic material to be readily transfected into the cells.

One example of gene editing is clustered regularly interspaced short palindromic repeats (CRISPR)-CRISPR associated protein 9 (Cas9), which is a recent technology that is proving to be faster, cheaper, more accurate, and more efficient than other existing gene editing methods. Details of the CRISPR-Cas9 approach is disclosed in U.S. application Ser. No. 13/842,859 filed Mar. 15, 2013 and published as US2014/0068797, the specifications of which are incorporated herein by reference. Briefly, a DNA-targeting RNA comprising a targeting sequence and bound to an enzymatically inactive Cas9 polypeptide exhibiting site-directed enzymatic activity determined by the DNA-targeting RNA are used for site-specific (target) modulation of a target nucleic acid in a target cell. The DNA-targeting RNA and Cas9 complex is introduced into the target cell and contacts the target DNA. Droplet microfluidics may be utilized to introduce said DNA-targeting RNA and Cas9 complex into the cell. The targeting sequence of the RNA molecule is complementary to a target sequence within the target DNA, thus targeting the Cas9 polypeptide to a specific location within the target DNA (the target sequence). The Cas9 polypeptide exhibits nuclease activity to cleave target DNA at the target DNA sequence, thus producing double strand breaks, which are then repaired by the cell, thus leading to modification of the gene such as, for example, gene correction, gene replacement, gene tagging, gene insertion, gene deletion, gene mutation, gene disruption, gene knock-out, gene knock-in, etc.

Here, the present invention provides an efficient and consistent lipofection platform for hard-to-transfect suspension cells via a single-cell, droplet-microfluidics approach: individual cells were co-encapsulated with cationic lipids and plasmids or vectors of the DNA-targeting RNA and Cas9 complexes in monodisperse microdroplets, and then subjected to chaotic advection in a winding channel.

SUMMARY OF THE INVENTION

It is an objective of the present invention to provide microfluidic systems and methods for transfection using microdroplets encapsulating cells, as specified in the independent claims. Embodiments of the invention are given in the dependent claims. Embodiments of the present invention can be freely combined with each other if they are not mutually exclusive.

In some aspects, the present invention features an on-chip, droplet-based, single-cell (or low cell number) transfection platform. In a microfluidic chip platform, cells (e.g., single cells) can be encapsulated in monodispersed microdroplets together with a transfection reagent (e.g., cationic lipids, cationic polymers) and one or more transfection molecules (e.g., plasmids, DNA-targeting RNA and Cas9 complexes or encoding vectors, etc). Droplet chaotic advection induced by a serpentine microchannel in a rendering channel of the platform results in a more uniform lipid-DNA complex (lipoplex) formation, which helps improve gene delivery efficacy. The rapid mixing of droplet contents by chaotic advection in the winding channels enables reagents to have a higher chance of collision and allows complete mixing in sub-millisecond timescales. Furthermore, the shear stress exerted on cell membranes during the chaotic mixing increases membrane permeability, which when combined with the co-confinement of cell and lipoplex, improves transfection efficiency. The methods and systems of the present invention may be used for a variety of applications such as gene therapy, RNA sequencing, in vitro fertilization, regenerative medicine, cancer treatment, vaccines, and gene editing etc.

According to some embodiments, a microfluidic system for cell transfection and gene editing may comprise a microfluidic device. The device may comprise a first aqueous phase channel comprising a first aqueous solution flowing through said first aqueous phase channel, a second aqueous phase channel comprising a second aqueous solution flowing through said second aqueous phase channel, and a combining channel having an inlet end and a tapering shearing outlet end. The first aqueous phase channel and the second aqueous phase channel may be fluidly connected to the inlet end of the combining channel. The first aqueous solution and second aqueous solution are co-flowing at the shearing outlet end of the combining channel. In some embodiments, the first aqueous solution may comprise cells and transfection molecules for CRISPR-CAS9. In other embodiments, the second aqueous solution may comprise transfection reagents. Examples of CRISPR-CAS9 transfection molecules include, but are not limited to, DNA vector encoding single guide RNA (sgRNA), a DNA vector encoding CAS9 nuclease gene, a DNA vector encoding both sgRNA and CAS9 nuclease gene, an sgRNA or other RNA molecule, a CAS9 nuclease or other protein molecule, an sgRNA-CAS9 complex, or other DNA or RNA and protein complex.

In further embodiments, the device includes a continuous phase channel network comprising a first continuous phase channel, a second continuous phase channel, and a continuous phase fluid that flows through each continuous phase channel; a droplet shearing junction formed by the outlet end of each continuous phase channel fluidly connecting to the shearing outlet end of the combining channel; and a rendering channel having an inlet end fluidly connected to the droplet shearing junction. The continuous phase fluid flowing through each of the continuous phase channels can combine at the droplet shearing junction and subsequently flow into the rendering channel. Preferably, at least a section of the rendering channel comprises a winding serpentine channel. In still further embodiments, the device includes the mono-dispersed droplets formed by the combining of the continuous phase fluid shearing the co-flowing aqueous solutions as the solutions exit the shearing outlet end of the combining channel. Each droplet may comprise and encapsulate at least one cell, at least one CRISPR-CAS9 transfection molecule, and at least one transfection reagent.

In preferred embodiment, the droplets flow through the rendering channel such that upon flowing through the winding serpentine channel portion, the droplets experience i) chaotic advection to form a lipoplex comprising the CRISPR-CAS9 transfection molecule and transfection reagent, and ii) shear stress applied to the cells, which increases membrane permeability of the cell, thus allowing for the lipoplex to enter the cell. In accordance with CRISPR-Cas9 techniques, the CRISPR-CAS9 transfection molecule is configured to modify a gene when transfected into the cell. The CRISPR-CAS9 transfection molecule may have a targeting sequence, or alternatively encode a targeting sequence, that is complementary to a target DNA sequence in the gene. The interaction of the targeting sequence with the target DNA sequence guides a Cas9 nuclease to the target sequence. The Cas9 nuclease then cleaves the target DNA at the target sequence to produce double strand breaks, which are repaired by the cell, thus leading to modification of the gene.

According to other aspects, the present invention features a microfluidic system for cell transfection. The system may comprise a first aqueous phase channel, where a first aqueous solution comprising cells and transfection molecules flows through the first aqueous phase channel; a second aqueous phase channel, where a second aqueous solution comprising transfection reagents flows through the second aqueous phase channel; and a combining channel having an inlet end and a shearing outlet end, where the first aqueous phase channel and the second aqueous phase channel are fluidly connected at least at the inlet end of the combining channel. The device further includes a continuous phase channel network comprising a first continuous phase channel and a second continuous phase channel, where a continuous phase fluid flows through each continuous phase channel. An outlet end of each continuous phase channel may be fluidly connected to the shearing outlet end of the combining channel thus forming a droplet shearing junction. In preferred embodiments, a rendering channel may have an inlet end fluidly connected to the droplet shearing junction and at least a section of the rendering channel may comprise a winding serpentine channel.

In some embodiments, the continuous phase fluid flowing through each of the continuous phase channels can recombine at the droplet shearing junction and subsequently flows into the rendering channel. The first aqueous solution and second aqueous solution are co-flowing at the shearing outlet end of the combining channel. As the co-flowing aqueous solutions exit the shearing outlet end of the combining channel, the recombination of the continuous phase fluid shears the co-flowing aqueous solutions to form monodispersed droplets in which at least one cell and at least one transfection molecule and at least one transfection reagent are encapsulated by each droplet. The droplets flow through the rendering channel such that upon flowing through the winding serpentine channel portion, the droplets experience chaotic advection that causes the transfection molecule and transfection reagent to form a lipoplex, and further causes shear stress to be applied to the cells, which increases membrane permeability, thus allowing the lipoplex to enter the cell.

In some embodiments, the shearing outlet end is tapered. In some embodiments, the first continuous phase channel and the second continuous phase channel are disposed on opposing sides of the combining channel. A section of the first continuous phase channel connected to the shearing outlet end and a section of the second continuous phase channel connected to the shearing outlet end may be orthogonal to the combining channel. In other embodiments, the rendering channel is fluidly connected to the outlet ends of the continuous phase channels. In one embodiment, the inlet end of the rendering channel has an arrowhead-shape such that the inlet end tapers at the droplet shearing junction, gradually widens, and then abruptly narrows as it transitions to a straight portion of the rendering channel.

In some embodiments, the fluid flow in the microfluidic device is pressure-driven. For example, the microfluidic device may further include a microfluidic pump operatively connected to at least one of the channels. In some embodiments, the microfluidic pump may be a pneumatic pump.

In some embodiments, the continuous phase fluid may comprise an oil. In other embodiments, the transfection reagents may comprise one or more species of cationic lipids. In yet other embodiments, the transfection reagents may comprise one or more species of cationic lipids and a helper lipid.

In some embodiments, the cells may be eukaryotic cells, prokaryotic cells, or a combination thereof. In one embodiment, the eukaryotic cells may be animal cells, plant cells, algae cells, fungal cells, or a combination thereof. In another embodiment, the prokaryotic cells are bacterial cells. In other embodiments, the cells may be protoplasts, pollen grains, microspores, tetrads, or a combination thereof.

Non-limiting examples of the transfection molecules include DNA, RNA, protein, a carbohydrate, a small molecule, or a combination thereof. In an exemplary embodiment, the transfection molecules may comprise CRISPR-CAS transfection molecules, such as for example, a DNA vector encoding single guide RNA (sgRNA), a DNA vector encoding CAS nuclease gene, a DNA vector encoding both sgRNA and CAS nuclease gene, an sgRNA or other RNA molecule, a CAS nuclease or other protein molecule, an sgRNA-CAS complex, or other DNA or RNA and protein complex. The CRISPR-CAS transfection molecule is configured to modify a gene by using its targeting sequence, or alternatively generating a targeting sequence, that is complementary to a target DNA sequence in the gene. When the targeting sequence interacts with the target DNA sequence, a CAS nuclease is guided to the target sequence and cleaves the target DNA at the target sequence to produce double strand breaks, which are repaired by the cell, thus leading to modification of the gene. In accordance with the mechanisms of CRISPR-CAS, the CRISPR-CAS transfection molecules can modify a gene via addition, deletion, replacement, or mutation.

According to other aspects, the present invention provides a method of transfecting cells. In some embodiments, the method may comprise providing any one of the microfluidic systems described herein, introducing the first aqueous solution and the second aqueous solution into their respective aqueous phase channel, combining the first aqueous solution and the second aqueous solution at the combining channel, introducing the continuous phase fluid into each of the continuous phase channels, combining the continuous phase fluids with the combined aqueous solutions at the droplet shearing junction, thereby shearing the aqueous solutions to form mono-dispersed microdroplets, each co-encapsulating at least one cell, at least one transfection molecule, and at least one transfection reagent, and flowing the microdroplets through the rendering channel. The flow of the microdroplets through the winding serpentine channel can induce chaotic advection that causes the transfection molecules and transfection reagents to form lipoplexes, and applies shear stress to the cells, thereby increasing membrane permeability to allow for transport of the lipoplexes through the cell membrane, thus transfecting the cells. In some embodiments, the method may be used in gene therapy, RNA sequencing, gene editing, development of regenerative medicine, cancer treatments, or vaccines, in vitro fertilization, in vitro assay, and the like.

As will be further described herein, the microfluidic platform of the present invention can improve the transfection efficiency, which was examined by the delivery of pcDNA3-EFGP (enhanced green fluorescence protein) plasmid, from ~5% to ~50% for all the three tested suspension cell lines, i.e., K562 (human chronic myelogenous leukemia cell line), THP-1 (human acute monocytic leukemia cell line), Jurkat (human acute T cell leukemia cell line), with significantly reduced cell-to-cell variation, compared to the bulk method. Cell membrane permeability may be increased by the shear stress exerted on the single cells as they individually passed through a droplet pinch-off junction and a winding rendering channel. Efficient targeted-gene knock-out of TP53BP1 for K562 cells via a CRISPR-Cas9 mechanism was also achieved using this platform. Lipoplex-mediated single-cell transfection via droplet microfluidics can have broad applications in gene therapy and regenerative medicine by providing high transfection efficiency and low cell-to-cell variation for hard-to-transfect suspension cells. As compared to conventional methods of gene transfection that require complicated operational procedures or have low transfection efficiency/accuracy or damage cell viability, the present invention provides a precise, safe, and efficient transfection system that has better transfection efficiency and consistency.

Without wishing to limit the invention to a particular theory, mechanism, or configuration, the microfluidic platform of the present invention can have a higher transfection efficiency and much lower transfection variability (higher consistency). For example, in some embodiments, the transfection efficiency of the present invention may be 10× higher that other existing platforms. These advantageous features may arise from the chaotic mixing that generates monodisperse lipoplexes in the proper size range for endocytosis, and the co-confinement of a single-cell with lipoplexes in a picoliter-droplet plus chaotic advection to overcome the diffusion limitations in the bulk reaction volume. Furthermore, the droplet shearing junction can have a slanted opening followed by a sharp constriction at the droplet pinch-off to confine the shear stress during droplet production in the dripping regime. This configuration may further contribute to the advantages of the invention by producing lipoplex that are substantially uniform in size, and by increasing membrane permeability due to cell deformation resulting from the exerted shear stress as the cell passes through the droplet pinch-off orifice.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 2A shows chaotic mixing of dye and PBS during droplet advection in the winding channel. FIG. 2B shows DLS size measurement of lipoplexes generated by droplet mixing using the present platform as compared to conventional vortexing. FIG. 2C is a fluorescence intensity histogram of 1,000 live single K562 cells analyzed via flow cytometry 48 h after transfection with pcDNA3-EGFP plasmid using droplet microfluidics-prepared and vortexing-prepared lipoplexes. FIG. 2D shows average lipofection efficiencies of K562 cells, as indicated by the percentages of EGFP positive cells, transfected via bulk lipofection protocol using either vortexing-prepared (▨) or droplet microfluidics-prepared (▧) lipoplexes, and via droplet lipofection using either a straight mixing channel (▦) or a winding mixing channel (▨) FIG. 2E is a numerical simulation showing symmetric and steady vortices when droplets move in the straight channel.

FIGS. 2H-2I shows cell deformation after experiencing shear stress when squeezing through the droplet generation pinch-off. FIG. 2H shows time-lapse micrographs showing the deformation of a K562 cell when it passed through the pinch-off of the flow-focusing droplet generation orifice. The pictures were taken at a frame rate of 45,000 pictures-per-second. FIG. 2I shows time-lapse images showing the shear stress at the pinch-off during the droplet generation calculated by numerical simulation. Scale bar: 50 μm.

FIG. 4A is a schematic illustration of the targeted gene knockout via the CRISPR/CAS9 mechanism. FIG. 4B is an annotated sequence map of the pLentiCRISPR.v2-sgTP53BP1 plasmid constructed for targeted knockout of the TP53BP1 gene in K562 cells. FIG. 4C shows an sgRNA sequence (SEQ ID NO: 1) and PAM sequence (SEQ ID NO: 2) targeting the 2nd exon of the TP53BP1 gene. FIG. 4D shows representative RT-qPCR amplification curves of every 1,000 K562 cells after the TP53BP1 knockout by either droplet lipofection or bulk lipofection. The Ct value of the bulk-lipofection group was very close to that of the non-transfected group, whereas the Ct value of the droplet-lipofection group was significantly higher, indicating a higher efficiency of gene knockout.

In FIGS. 7A-7C, the RT-qPCR amplification curves of every 1,000 K562 cells after the TP53BP1 knockout by either droplet lipofection or bulk lipofection in three repeating experiments. The Ct value of the bulk-lipofection group was very close to that of the non-transfected group, whereas the Ct value of the droplet-lipofection group was significantly higher, indicating a higher efficiency of gene-knockout. FIG. 7D shows a standard curve for calibrating the absolute number of TP53BP1 mRNA molecules.

DETAILED DESCRIPTION OF THE INVENTION

Figure 1A:
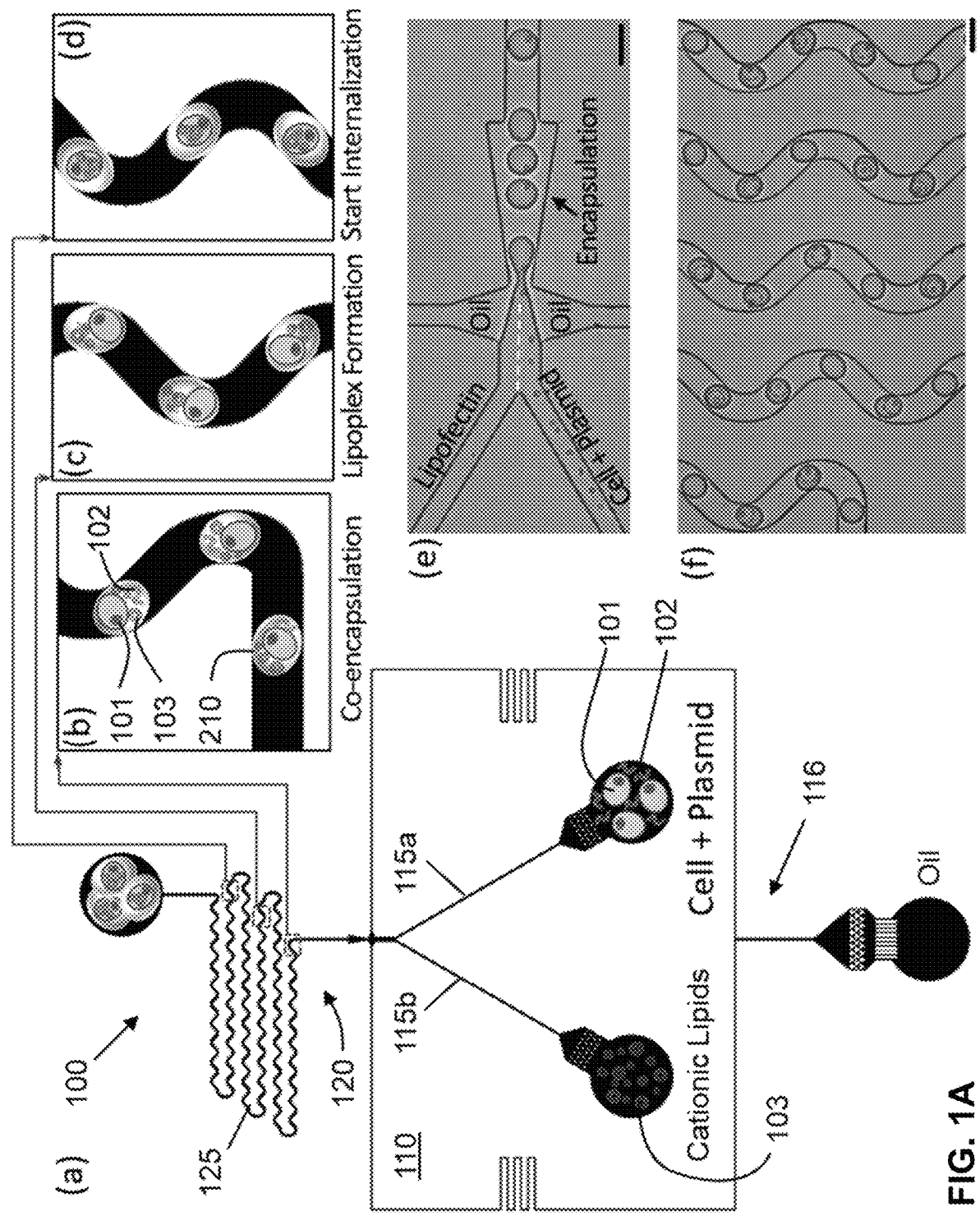
FIG. 1A is a schematic view and mechanism of a system of the present invention. Section (A) shows a schematic illustration of the droplet microfluidics-based single-cell lipofection platform. The zoom-in views of the circled regions are shown in the upper right corner: a single-cell is co-encapsulated with plasmid and Lipofectin® is shown in section (B), thereafter negatively-charged plasmid and positively-charged Lipofectin self-assemble into lipoplex during chaotic advection as shown in section (C), which enters the co-encapsulated single cell by endocytosis shown in section (D).

Following is a list of elements corresponding to a particular element referred to herein:
- 100 microfluidic system
- 101 cells
- 102 transfection molecules
- 103 transfection reagents
- 110 microfluidic chip/device
- 115a first aqueous phase channel
- 115b second aqueous phase channel
- 116 continuous phase channel network
- 117a first continuous phase channel
- 117b second continuous phase channel
- 118 combining channel
- 120 rendering channel
- 125 serpentine/winding channel portion
- 205 droplet shearing junction
- 210 droplets According to some embodiments, the present invention features methods and systems for efficient and consistent transfection through co-encapsulation of single cells, transfection molecules such as plasmids and DNA-targeting RNA and Cas9 complexes, and transfection reagents such as cationic lipids and cationic polymers, into monodispersed microdroplets and rapid mixing by chaotic advection.

Transfection Reagents

The methods and systems of the present invention feature the use of transfection reagents, which are co-encapsulated with cells and transfection molecules (e.g., plasmids, DNA-targeting RNA and Cas9 complexes or encoding vectors etc.) in microdroplets. In some embodiments, the transfection reagents comprise cationic lipids. Cationic lipids or other appropriate lipid aggregates can function to facilitate introduction of macromolecules, such as DNA, RNA, and proteins, into living cells. Since the membranes of most cells have a net negative charge, cells do not readily take up anionic molecules, particularly those of high molecular weight. Cationic lipids aggregate to and bind polyanions, such as nucleic acids, tending to neutralize the negative charge. The effectiveness of cationic lipids in transfection of nucleic acids into cells is thought to result from an enhanced affinity of cationic lipid-nucleic acid aggregates for cells, as well as the function of the lipophilic components in membrane fusion.

Cationic lipids, which are amphiphilic molecules with cationic groups in the head group, are well known to one of ordinary skill in the art. One well-known example is Lipofectamine®. Other examples include poly-1-lysine (PLL) and polyethyleneimine (PEI). The present invention is not limited to the aforementioned cationic lipids or other commercially available cationic lipids (e.g., Lipojet™, LipoD293™, etc.), as any appropriate cationic lipid may be considered, e.g., glycerol derived lipids, cholesterol derived lipids, pyridine derived lipids, malonic acid derived lipids, etc. In some embodiments, the transfection molecule comprises cationic lipids and one or more helper molecules (e.g., helper lipids).

Transfection Molecules

Nucleic acid, e.g., DNA or RNA, is the most commonly transfected molecule. However, the present invention is not limited to transfection of DNA or RNA. In some embodiments, the molecule that is transfected is DNA, RNA, a protein, a carbohydrate, a small molecule (e.g., a drug), the like, or a combination thereof. In some other embodiments, the transfection molecule may be a targeting complex comprising a DNA-targeting RNA bound to Cas9 polypeptide, also referred to as a Cas9 nuclease, which forms a DNA-targeting RNA and Cas9 complex. The Cas9 may be naturally-occurring, a derivative, or modified Cas9. In other embodiments, the transfection molecule may be a targeting complex comprising a DNA-targeting RNA bound to a site-active polypeptide other than Cas9. In other embodiments, the transfection molecule may be a targeting complex that can be used in CRISPR-Cas gene editing. For example, the transfection molecule is the DNA-targeting RNA and Cas9 complex for CRISPR-Cas9. In some other embodiments, the transfection molecule for CRISPR-CAS9 may be a DNA vector encoding sgRNA, a DNA vector encoding CAS9 nuclease gene, DNA vector encoding both sgRNA and CAS9 nuclease gene, an sgRNA or other RNA molecules, a CAS9 nuclease or other protein molecules, an sgRNA-CAS9 complexes, or other DNA or RNA and protein complex.

Transfected Cells

Any particular cell type from any organism may be used in the methods and systems of the present invention, namely any cell suitable for transfection. In some embodiments, the cells may be wild type cells or genetically modified cells. In other embodiments, the cells may be cells harboring one or more mutations, healthy cells, diseased cells or unhealthy cells, etc. For example, in some embodiments, the cells may be prokaryotic cells (e.g., bacteria, archaebacteria, etc.). In other embodiments, the cells may be eukaryotic cells such as single-celled eukaryotes, fungal cells (e.g. yeast, mold, etc.), animal cells, mammalian cells (e.g. cells from a human, non-human primate, rodent, rabbit, sheep, dog, cat, etc), and non-mammalian cells (e.g. cells from insects, reptiles, amphibians, birds, etc.).

In some embodiments, the cells used in the present invention may be other eukaryotic cells such as plant cells or algal cells. Non-limiting and non-exhaustive examples of plant cells include cells from corn, soybean, wheat, cotton, grass, flowering plants, fruit-bearing plants, trees, tuberous plants, potatoes, root plants, carrots, peanut, nuts, beans, legumes, and squashes. It is to be understood that the term "plant cell" encompasses all types and stages of plant cells and is not limited to the aforementioned examples. Non-limiting and non-exhaustive examples of algal cells include cells from *Chlorella* sp., *Nannochloropsis* sp, and *Botryococcus* sp. It is to be understood that the term "algal cell" encompasses all types of algal cells and is not limited to the aforementioned examples. One of the distinguishing characteristics that plant and algal cells have over animal cells is a cell wall that surrounds a cell membrane to provide rigidity, strength, and structure to the cell. The cell wall may be comprised of polysaccharides including cellulose, hemicellulose, and pectin. Similar to plant and algal cells, the fungal cells also have a cell wall, which may be comprised of polysaccharides including glucans, mannans, and chitin. In some embodiments, the microfluidic systems and methods described herein may allow for transfection through the cell wall as well as the cell membrane.

In other embodiments, the cells used in the present invention may be protoplasts, which are intact plant, bacterial or fungal cells that had its cell wall completely or partially removed using either mechanical or enzymatic means.

In yet other embodiments, the cells used in the present invention may be a tetrad. The term "tetrad" is used to herein to refer to a single structure comprised of four individual physically attached components. A "microspore" is an individual haploid structure produced from diploid sporogenous cells (e.g., microsporoyte, pollen mother cell, or meiocyte) following meiosis. A microspore tetrad refers to four individual physically attached microspores. A "pollen grain" is a mature gametophyte containing vegetative (non-reproductive) cells and a generative (reproductive) cell. A pollen tetrad refers to four individual physically attached pollen grains.

Methods and Systems for Transfection

Referring to FIG. 1A, the present invention features a microfluidic system (100) for cell transfection. According to some embodiment, the system (100) may comprise a microfluidic chip (110) with a first aqueous inlet channel (115a) and a second aqueous inlet channel (115b). The first aqueous inlet channel (115a) and second aqueous inlet channel (115b) fluidly connect into a central combining channel (118). Cells (101) and plasmids (102) are suspended in a buffer (e.g., Opti-MEM reduced serum buffer) and are introduced into the microfluidic chip (110) via the first aqueous inlet channel (115a). Cationic lipids (103) (e.g., Lipofectamine®, Lipojet™, LipoD293™, etc.) are introduced to the microfluidic chip (110) via the second aqueous inlet channel (115b). The chip (110) further comprises at least one continuous phase inlet channel (116) that fluidly connects to a terminal end of the central combining channel (118), thus forming a droplet shearing junction (205). In some embodiments, the continuous phase may comprise oil, such as mineral oil or alternative to mineral oil. At the shearing junction (205), the continuous phase shears the two co-flowing aqueous phases (the cells (101)/plasmids (102) and the cationic lipids (103)), generating single-cell encapsulating droplets (210).

Figure 1B:
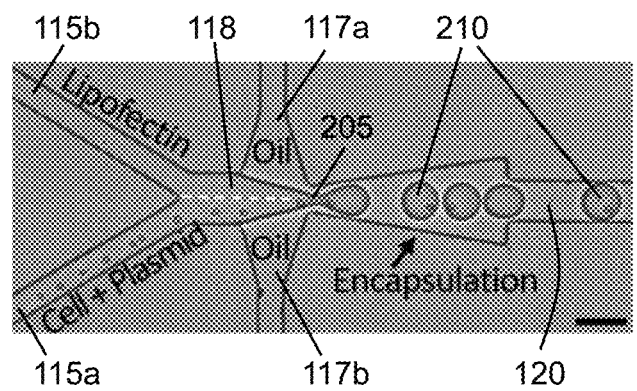
FIG. 1B shows droplet generation and co-encapsulation of single K562 cells with plasmids and Lipofectin in picoliter-droplets. Scale bar: 100 μm.

In some embodiments, the encapsulating droplets (210) subsequently enter into a rendering channel (120). In one embodiment, as shown in FIG. 1B, an inlet end of the rendering channel has an arrowhead-shape such that the inlet end tapers at the droplet shearing junction, gradually widens, and then abruptly narrows to a width of a straight portion of the rendering channel. The width of the straight portion is sufficient to allow for the droplets to enter the straight portion. The rendering channel further comprises a serpentine channel portion (125), in which chaotic advection induces rapid mixing and shear, resulting in lipoplex formation and transfection of the cell. In some embodiments, the system can be implemented in gene therapy, RNA sequencing, development of regenerative medicine, cancer treatments, or vaccines, in vitro fertilization, or an in vitro assay.

In some embodiments, the system (100) of the present invention may be constructed from a variety of materials. For example, in some embodiments, the system (100) is constructed from a material comprising a polymer, a plastic, glass, the like, or a combination thereof. As a non-limiting example, in some embodiments, the system (100) comprises a polydimethylsiloxane (PDMS) based microfluidic chip fabricated using standard soft-lithography methods with an SU8 master mold on a silicon substrate generated by photolithography. The system (100), e.g., the microfluidic chip (110), may be constructed with any appropriate material.

The present invention is not limited to a single unit (e.g., microfluidic chip). In some embodiments, the system may comprise a plurality of microfluidic chips, referred to as a microfluidic array. For instance, multiple experiments may be performed in parallel using the microfluidic array.

As used herein, the microfluidic devices employ fluid volumes on the scale of microliters ($10^{-6}$) to picoliters ($10^{-12}$) that are contained within sub-millimeter scale channels. The structural or functional features may be dimensioned on the order of mm-scale or less. For example, a diameter of a channel or dimension of a chamber may range from <0.1 µm to greater than 1000 µm. Alternatively or in addition, a length of a channel may range from 0.1 µm to greater than cm-scale. Alternatively or in addition, the serpentine channel section may comprise two or more winding turns. For example, the serpentine channel section may comprise 2 to 20 winding turns.

As previously discussed, the methods and systems of the present invention provide a more uniform formation of lipoplex using chaotic mixing inside mono-dispersed microdroplets compared to lipoplex formation using vortexing or hand-shaking. Without wishing to limit the present invention to any theory or mechanism, it is believed that the uniform formation of lipoplex reduces the transfection variation between cells and improves the overall intracellular delivery efficiency. Further, the co-confinement of a single cell and the lipoplex in microdroplets helps to breaks the diffusion limitation in bulk transfection so that the cell and lipoplex are in closer contact. Further still, the shear stress exerted on the cell membrane during the chaotic advection helps improve the membrane permeability. The entire process is cell-friendly; neither genomic disruption nor viability damage is applied to cells.

Experimental Example

The following is a non-limiting example of the present invention, in particular, to a microfluidic system and use thereof. The example is for illustrative purposes only and not intended to limit the invention in any way. Equivalents or substitutes are within the scope of the invention.

Chip Fabrication and Experimental Setup

The presented microfluidic device was fabricated via soft lithography. A 30-µm high SU-8 master mold was patterned on a silicon wafer using standard photolithography, whereafter liquid polydimethylsiloxane (PDMS) mixture comprising a base and curing agent at a 10:1 ratio was cast on the mold and cured for 3 h in a convection oven at 65° C. for complete cross-linking. The PDMS microchannel was then peeled off from the mold and irreversibly bonded to a clean glass slide after oxygen plasma treatment for 60 s. The sealed chip was baked at 120° C. overnight to secure the channel hydrophobicity. All the reagents were driven into the microfluidic chip through polymer tubing and syringe pumps.

Plasmid Preparation

A pcDNA3-EGFP vector (Addgene plasmid #13031) encoding enhanced green fluorescence protein (EGFP) was propagated in *Escherichia coli* (*E. coli*), extracted, and purified using the QIAprep Spin Miniprep Kit. The plasmid was dissolved in EB buffer and stored at −20° C. until use. For targeted gene knockout, a 20-bp sgRNA sequence targeting the 2nd exon of TP53BP1 is CAGAATCATCCT-CTAGAACC (SEQ ID NO: 1). This sgTP53BP1 sequence was cloned into a pLentiCRISPR v2 vector encoding the *S. pyogenes* Cas9 protein, and the re-constructed plasmid was purchased from GenScript. Every time before the transfection experiment, the plasmid concentration was measured by the absorbance at 260 nm using a NanoDrop Spectrophotometer.

Cell Culture and Lipofection

K562 (human chronic myelogenous leukemia cell line), THP-1 (human acute monocytic leukemia cell line), and Jurkat (human acute T cell leukemia cell line) cells were purchased from American Type Culture Collection (ATCC), and cultured in RPM11640 medium supplemented with 10% fetal bovine serum (FBS). 0.05 mM of 2-mercaptoethanol was added as a metabolic supplement for THP-1 cell culture. HeLa cells were purchased from ATCC and cultured in DMEM medium supplemented with 10% FBS. Cells were cultured in a humidified incubator at 37° C. with 5% $CO_2$, and passaged every 2-3 days following standard protocols. A day before transfection, cells were re-suspended in 10 mL fresh media at $5 \times 10^5$ viable cells/mL in a T-75 flask, to maintain the cells in the logarithmic (Log) growth phase.

Before transfection, cells were washed once with Opti-MEM reduced serum medium and re-suspended in Opti-MEM at $10^7$ cells/mL. For lipofection via droplet microfluidics, the cell suspension was added with 2 µg per 100 µL of pcDNA3-EGFP plasmid and introduced into the microfluidic chip via one inlet; cationic lipid Lipofectin® was diluted in Opti-MEM at a concentration of 4 µL per 100 µL and introduced through the other inlet. The two co-flowing aqueous phases were sheared by FC-40 (Fluorinert™) with 5% 1H, 1H, 2H, 2H-perfluoro-1-octanol into single-cell encapsulating droplets and experienced chaotic mixing in the winding channel. The emulsion was collected and centrifuged at 500 rpm for 30 s to separate the aqueous phase containing cells and lipoplexes from the oil phase. For lipofection via the conventional bulk method, DNA suspension (2 µg DNA per 100 µL Opti-MEM) was added to the Lipofectin® suspension (4 µL Lipofectin® per 100 µL Opti-MEM), gently vortexed and added to the cell suspension. For both of the lipofection methods, the cells and lipoplexes were incubated at 37° C., 5% $CO_2$ for 24 h, and thereafter, the cells were re-suspended in complete growth media for another 24 h before transgene expressing investigation.

Flow Cytometry

For quantitative analysis of the transfection efficiency and the cell viability, cells were washed and re-suspended in PBS supplemented with 2% FBS at a concentration of $2 \times 10^7$ cells/mL 48 h after initial experiment. 1 µg/mL propidium iodide was added for dead cell staining. The cell suspension was analyzed using the ImageStream Mark II Imaging Flow Cytometer at 60× magnification under the laser excitation of 488 nm, 150 mW. The data containing the single-cell bright-field and fluorescent images of each individual cell were analyzed using the IDEAS® software package.

Setup of the Reverse Transcription-Quantitative Real-Time PCR (RT-qPCR)

The *S. pyogenes* Cas9 enzyme generates double-strand breaks at the single guide RNA (sgRNA) targeted locus, which can lead to gene knockout so that the mRNA at this locus will not be transcribed. Here, the TB53BP1 knockout efficiency was analyzed by RT-qPCR using the Cells-to-CT™ 1-Step Power SYBR® Green Kit following the manufacturers protocol. Firstly, 1,000 transfected K562 cells were lysed in the lysing buffer. Thereafter, for a reaction volume of 20 µL, 2 µL cell lysate, 10 µL qRT-PCR Mix, 0.16 µL RT Mix, 200 nM forward primer, and 200 nM reverse primer were added. A Chromo4 qPCR instrument was used with the following thermal cycling setup: 48° C. for 30 min (reverse transcription), 95° C. for 10 min (polymerase activation), 45 cycles of 94° C. for 15 s and 60° C. for 1 min (amplification). Melting curves were generated by increasing the temperature from 60° C. to 95° C. and holding for 10 s after each 0.5° C. temperature increment. The forward primer sequence was 5'-GGTTCTAGAGGATGATTCTG-3' (SEQ ID NO: 3), and the reverse primer sequence was 5'-TTCAGG-ATTGGACACAAC-3' (SEQ ID NO: 4).

Numerical Simulation

Numerical modeling was adopted to analyze the chaotic mixing of droplets passing through the straight/winding channel, and the shear stress at the flow focusing droplet generation junction. 2D transient modeling of fluid flows for both analyses was performed using COMSOL Multiphysics. Specifically, the level-set multiphase model was employed to accurately track the interface between the aqueous and the oil phases. The density and viscosity of the oil phase were set as 1.855 g/mL and 3.40 mPa·s according to the propriety of FC-40; while the values of 1.007 g/mL and 0.74 mPa·s were chosen for the aqueous phase according to the property of Opti-MEM. The surface tension between the two phases and the contact angle were set at 0.01 N/m and 180°, respectively. Triangular mesh elements were mainly used for meshing the geometries. For analyzing the chaotic advection in the winding channel, a total of 100,000 triangular elements were used, whereas a total of 20,000 mesh elements were utilized to analyze the shear stress at the flow focusing droplet generation junction. For both analyses, the mesh was refined near the walls of the microchannel for better accuracy.

Platform Design

Figure 1C:
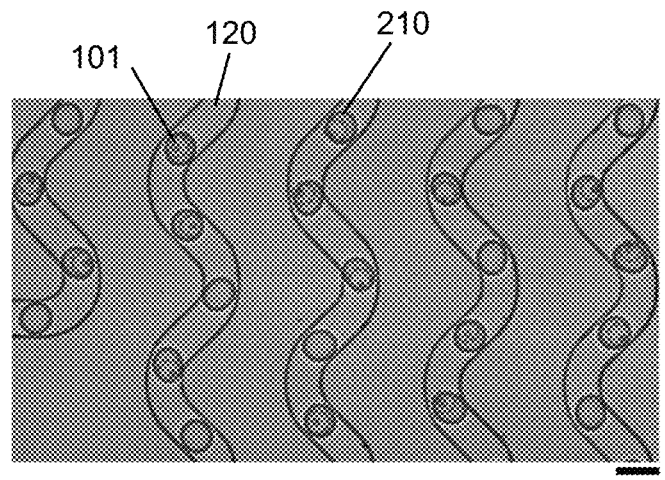
FIG. 1C shows a bright-field snap-shot of droplets' chaotic advection in the winding channel. The encapsulated single K562 cells are highlighted by red circles. Scale bar: 100 μm.

An embodiment of the droplet microfluidics-based single-cell lipofection platform of the present invention is illustrated in FIG. 1A, section (A). Two co-flowing aqueous phases, one for cell and plasmid suspension and the other for cationic lipid solution, are pinched off at a flow-focusing geometry. As shown in section (B), at this junction, single cells are co-encapsulated with cationic lipids and plasmids in monodisperse microdroplets and experience chaotic mixing in the winding channel. While undergoing chaotic mixing, plasmid and cationic lipid self-assemble into lipoplexes, as shown in section (C), which enter the co-encapsulated single cell through endocytosis, as shown in section (D). The concentrations of the suspension cells ($10^7$ cells/mL), plasmids (2 µg per 100 µL), and cationic lipids (4 µg per 100 µL) were set based on the manufacturer's protocol. A 1% (v/v) Pluronic F-68 was added to the cell suspension to avoid cell aggregation. The composition of the oil phase, FC-40 with 5% 1H, 1H, 2H, 2H-perfluoro-1-octanol (v/v), was optimized so that the droplets were able to stay apart during the chaotic advection, but were easy (500 rpm, 30 s) to fuse together and separate into two phases for cell and lipoplex collection. In some embodiments, fluorocarbon oil (i.e., FC-40) may be used as the encapsulation phase instead of hydrocarbon oil (e.g., mineral oil). Fluorocarbon oil has higher gas permeability and much lower solubility of organic molecules, which can permit high cell viability and minimal loss of the transfection reagents into the oil phase. At a flow rate of 1.2 µL/min for each of the two aqueous phases, and 6.0 µL/min for the oil phase, the resulting single cell-lipoplex co-encapsulating droplets had a diameter of 52 µm (FIG. 1B, 1C).

Droplet production was in the dripping regime with a production rate of 0.85 kHz, where droplet breakup was shear-dominated and the fluid interface was detached from the channel surface. Due to the limitation imposed by Poisson statistics for random cell loading, the single-cell encapsulation efficiency of the platform was about 18%. In alternative embodiments, a higher single-cell loading efficiency may be achieved if the platform is coupled with inertial cell ordering in a curved channel, or inertial cell focusing in a long, high-aspect-ratio microchannel, or one-cell-to-one-droplet releasing by the hydrodynamic microvortices at the droplet pinch-off interface.

The cationic lipid used herein is Lipofectin®, a non-viral vector for cell transfection, which comprises a mixture of positively charged lipid N-(1-(2,3-dioleyloxy)propyl)-n,n,n-trimethylammonium chloride (DOTMA), and helper lipid dioleoyl-phophotidylethanolamine (DOPE) at a 1:1 (w/w) ratio. Cationic lipids form lipoplexes spontaneously with polyanionic nucleic acids upon electrostatic interaction, and the resulting complexes interact with the cell membrane and are internalized through endocytosis. Upon endosomal maturation, a fraction of DNA escapes and enters the nucleus to elicit gene expression. Alternatively, DNA is degraded within the lysosome. The fusogenic behavior of DOTMA results in functional intracellular delivery of polynucleotide in a manner that bypasses degradative enzymes present in the lysosomal compartment. While DOPE facilitates the intracellular release of DNA, its amine group interacts with DNA phosphate groups, making the lipoplex more susceptible to disassembly; besides which, it rapidly fuses with the endosomal lipid bilayer, promoting DNA endosomal escape.

Chaotic Mixing in Microdroplets

Figure 1D:
FIG. 1D shows Fluo-4 emitting strong fluorescence after mixing with $Ca^{2+}$. Fluorescence intensity increased and eventually saturated during the droplet chaotic advection in the rapid mixing region.

Chaotic advection is induced in the unsteady, time-dependent flows inside the droplets moving through a winding microchannel of a rendering region, which results in rapid mixing on a millisecond timescale. As demonstrated in FIG. 1D, Fluo-4 and $Ca^{2+}$ were encapsulated and mixed by chaotic advection, emitting strong green fluorescence as the droplet moved along the rendering channel.

Due to the chaotic mixing inside micro-droplets, the lipoplexes generated from the platform were monodisperse with a mean diameter of 277 nm, which was in the proper size range for internalization by endocytosis. The avoidance of the non-uniformity of lipoplexes prepared via bulk preparing processes (e.g., hand shaking or vortexing) was confirmed by dynamic light scattering (DLS, FIG. 2B). As a result, the proportion of lipoplexes that were too large or too small for intracellular delivery was minimized. K562 cells were transfected with pcDNA3-EGFP plasmid using both droplet microfluidics-prepared lipoplexes and vortexing-prepared lipoplexes following the standard lipofection protocol, and analyzed by flow cytometry 48 h after transfection. As shown in the fluorescence intensity (x-axis) versus cell count (y-axis) histogram of every 1,000 live transfected K562 cells (FIG. 2C), cells transfected with droplet microfluidics-prepared lipoplexes demonstrated a clear shift towards a higher fluorescence intensity indicating a higher EGFP transfection efficiency, compared to cells transfected with vortexing-prepared lipoplexes. To compensate for auto-fluorescence, surface binding and endocytosis, the EGFP transfection threshold, i.e., the vertical line in the histogram, was defined such that less than 1% of cells in the negative control group (cells transfected with pcDNA3.1 plasmid, a vector without any fluorescence protein-encoding sequences, following the standard lipofection protocol) fell into the effective EGFP transfection region in the histogram (FIGS. 5A-5D). Based on three repeating experiments transfecting K562 cells following the standard lipofection protocol, the transfection efficiency was 9.0±1.2% when using droplet microfluidics-prepared lipoplexes, which was significantly higher than using vortexing-prepared lipoplexes (4.8±0.9%, FIG. 2D), verifying the importance of the lipoplex monodispersity on transfection efficiency.

To compensate for auto-fluorescence, surface binding, and endocytosis, K562, THP-1, Jurkat, and HeLa cells were transfected with pcDNA3.1 plasmid, a vector without any fluorescence protein-encoding sequences, following the standard lipofection protocol as the negative control, and analyzed via flow cytometry 48 h after transfection. The sample fluorescence intensity v.s. normalized cell-count frequency histograms of the 4 types of cells in the negative control group were shown in FIGS. 5A-5D. The EGFP transfection threshold (vertical line in the histogram) was defined such that less than 1% of cells in the negative control fell into the effective EGFP transfection region (unshaded region) in the histogram. The EGFP transfection efficiency of a sample thus corresponded to the percentage of live cells that were in the effective transfection region.

Figure 2A:
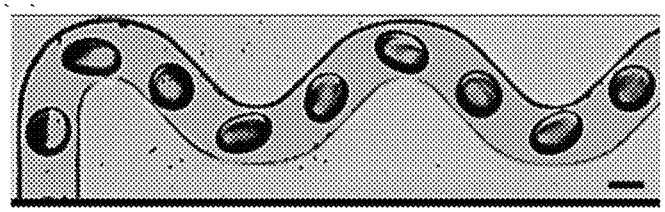
FIGS. 2A-2E shows mechanisms of improved transfection efficiency via droplet chaotic advection in the winding channel.
Figure 2B:
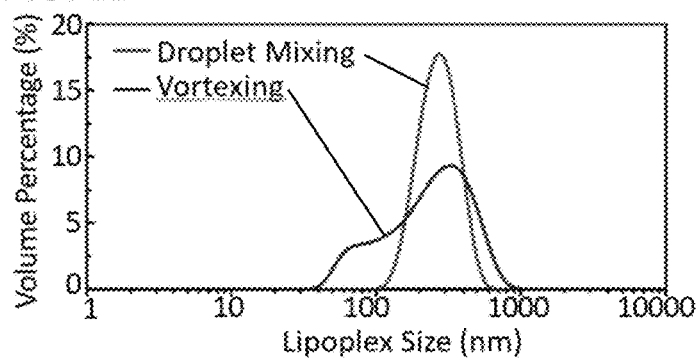
Figure 2C:
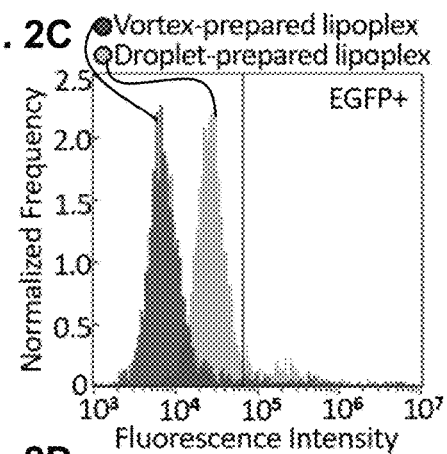
Figure 2D:
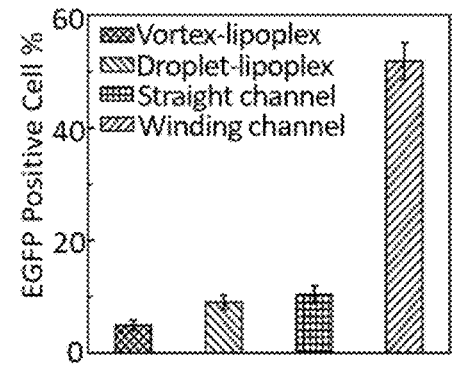
Figure 2E:
Figure 2F:
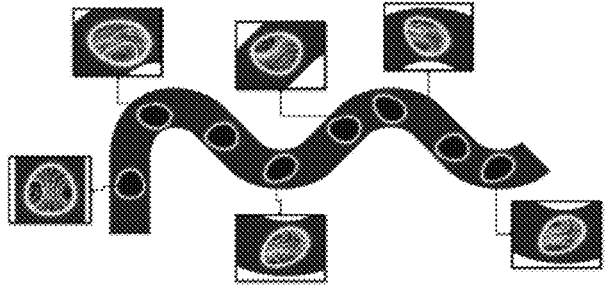
FIG. 2F is a numerical simulation illustrating asymmetric and constantly-changing vortices during droplet advection in the winding channel.
Figure 2G:
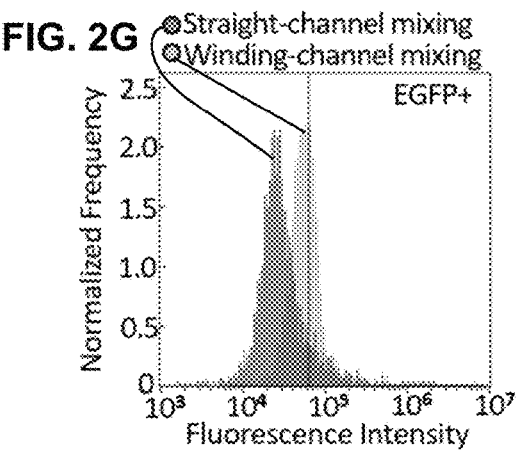
FIG. 2G shows a fluorescence intensity histogram of 1,000 live single K562 cells analyzed via flow cytometry 48 h after transfection with pcDNA3-EGFP plasmid using the present droplet-lipofection platform with a winding channel and a modified platform with an equal-length straight channel. Scale bar: 50 μm.
Figure 5A:
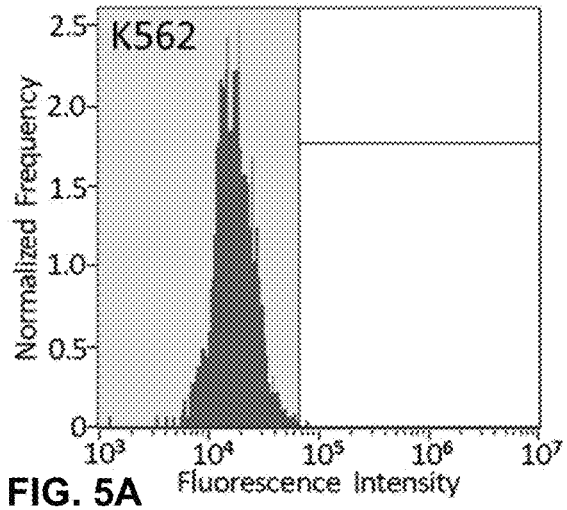
FIGS. 5A-5D show fluorescence intensity histograms from flow cytometry of K562 (FIG. 5A), THP-1 (FIG. 5B), Jurkat (FIG. 5C), and HeLa (FIG. 5D) cells in the negative control group.
Figure 5B:
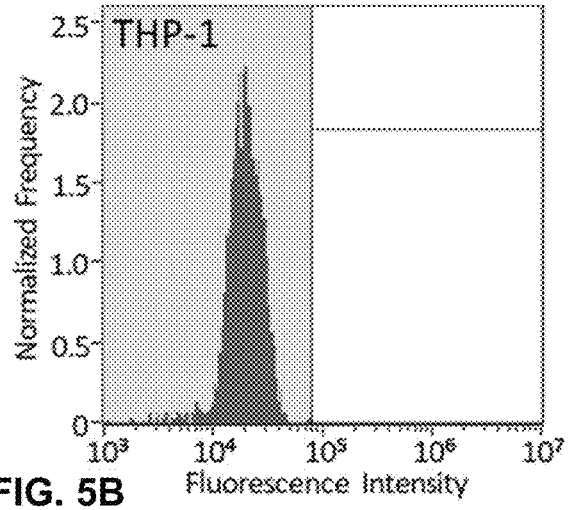
Figure 5C:
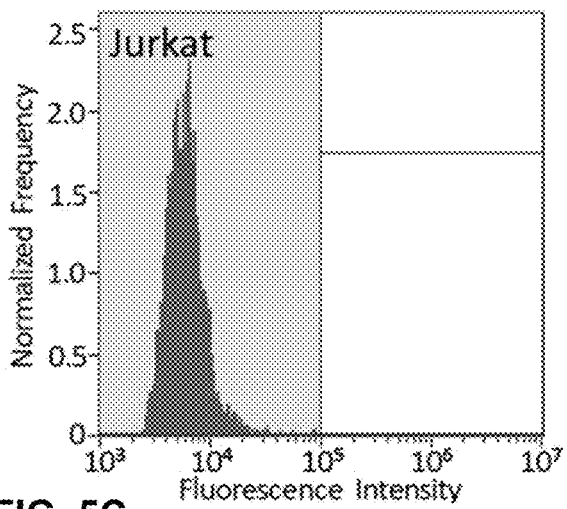
Figure 5D:
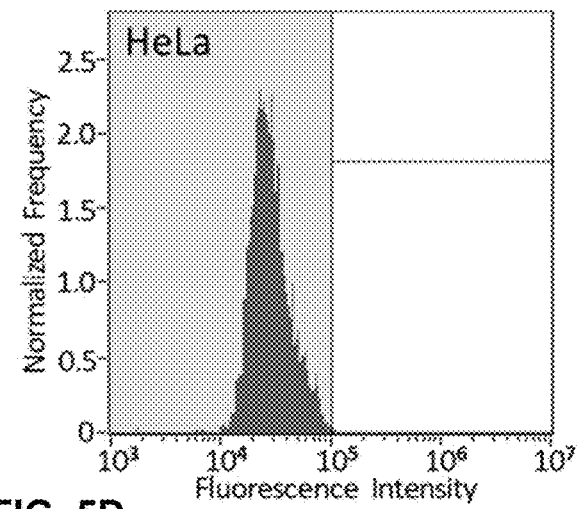
Figure 5E:
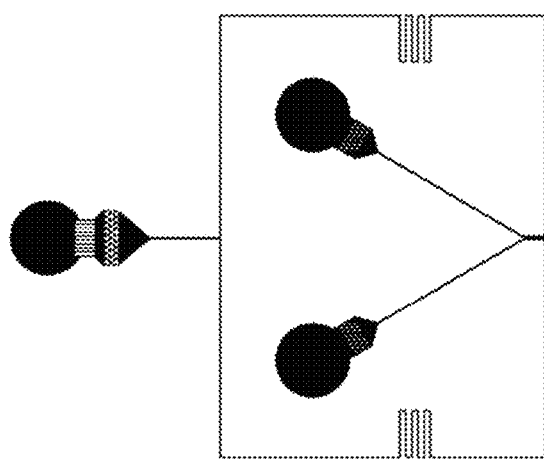
FIGS. 5E-5F show a non-limiting embodiment of the droplet-lipofection platform with a straight mixing channel (FIG. 5E) and droplets encapsulating single K562 cells and lipoplexes running through this straight channel (FIG. 5F). Scale bar: 100 μm.
Figure 5F:
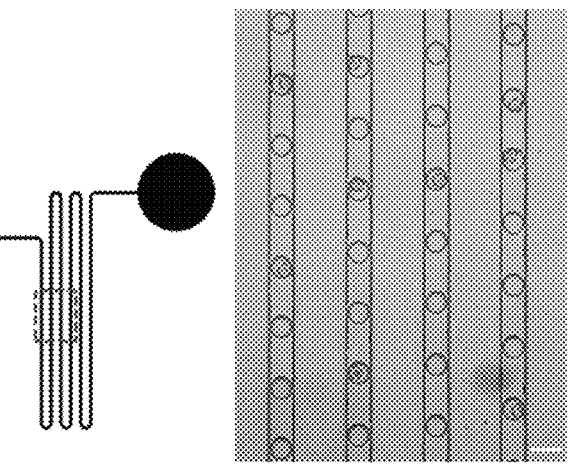

When a droplet is moving in a straight channel, due to the equal shearing interaction between the flow and the side walls, two steady and symmetrical vortices are induced within the left and the right (along the flow direction) halves of the droplet (FIG. 2E). This results in poor mixing since the streamlines from each half do not cross each other. However, when a droplet is moving in a winding channel, because of the asymmetric shear experienced by the droplet at each turning portion, two asymmetric vortices fold and stretch the fluid inside the droplet, as illustrated by numerical simulation (FIG. 2F). Thus, chaotic advection and rapid mixing occur inside droplets because crossing of the streamlines becomes possible at each turn. The effectiveness of chaotic advection can be quantified by striation thickness ($s_t$), the distance over which mixing has to occur by diffusion. For a droplet passing through a winding channel, the striation thickness decreases exponentially according to $s_t(n) = s_t(0) \times 2^{-n}$, as explained in the Baker's Transformation, where n is the number of stretching, folding and reorienting cycles, $s_t(0)$ is the initial striation thickness, and $s_t(n)$ is the striation thickness after n cycles. The chance of cell-lipoplex collision was significantly increased due to the confinement of a single cell with lipoplexes inside picoliter-volume micro-droplets and the intensive chaotic mixing, which overcame the diffusion limitations in the bulk volume. To compare the lipofection efficiency via droplet chaotic mixing in a winding channel versus droplet mixing in a straight channel, K562 cells were transfected with pcDNA3-EGFP plasmid using both the droplet-lipofection platform and a modified platform with the winding channel replaced by an equal-length straight channel (FIGS. 5E-5F). As shown in the flow cytometry histogram (FIG. 2G), the EGFP positive cells transfected via the platform with a straight mixing channel had a broader fluorescence intensity distribution, which was suggested to be caused by the insufficient droplet mixing. As shown in FIG. 2D, the transfection efficiency using the straight channel droplet-lipofection platform was 10.3±1.6%, which was higher than bulk lipofection (4.8±0.9%) but much lower than cells transfected through the present platform with a winding channel (51.8±3.3%). The results indicate that chaotic mixing in the winding channel is necessary for achieving the optimum transfection efficiency and consistency.

Cell Deformation at the Droplet Pinch-Off

As is shown in FIG. 2H, an originally round and spherical suspension cell was deformed and stretched after passing through the droplet generation pinch-off orifice in the platform, since it was exposed to rapid constriction and shear. The shear stress at the droplet pinch-off was as high as 514 dyne/$cm^2$ as calculated by numerical simulation (FIG. 2I).

Transient membrane disruptions or holes may be caused by the rapid mechanical deformation of a cell, as it passes through a constriction smaller than the cell diameter or is subjected to high shear stresses. The degree of disruption and the size and frequency of the holes are determined by the imposed shear and compressive forces. In the present platform, apart from deforming cells at the droplet pinch-off, cationic lipids were incorporated as the non-viral vector to facilitate the delivery of large protein-encoding plasmids with big backbones by lipoplex endocytosis. Among the three barriers of lipoplex-mediated gene delivery, i.e., the cell, endosomal and nucleus membranes, the present platform was capable of overcoming the cell membrane barrier by increasing membrane permeability through cell deformation at the droplet pinch-off.

Increased Transfection Efficiency and Consistency for Suspension Cells

Figure 3A:
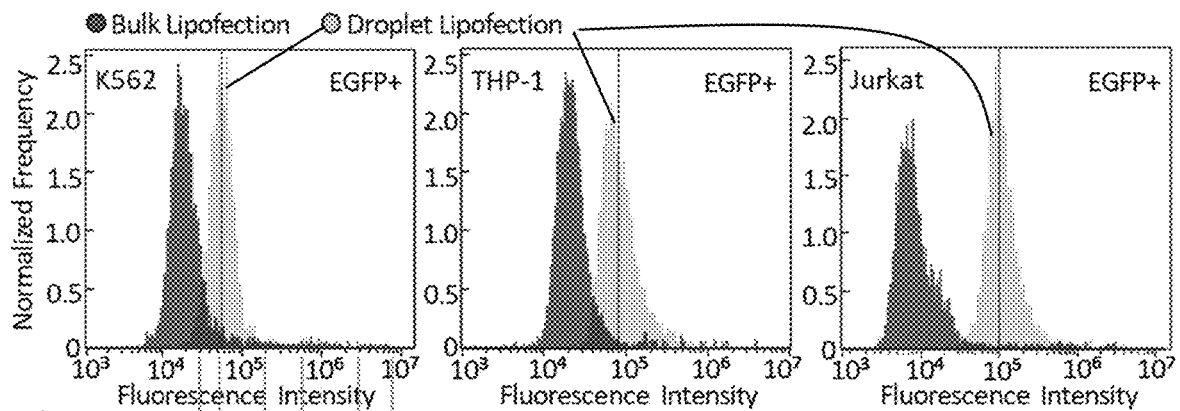
FIG. 3A shows fluorescence intensity of 1,000 live single K562 (left), THP-1 (middle), or Jurkat (right) cells analyzed via flow cytometry 48 h after transfection of pcDNA3-EGFP plasmid via either bulk incubation with vortexing-prepared lipoplex or the present droplet microfluidics-based single-cell lipofection platform.
Figure 6A:
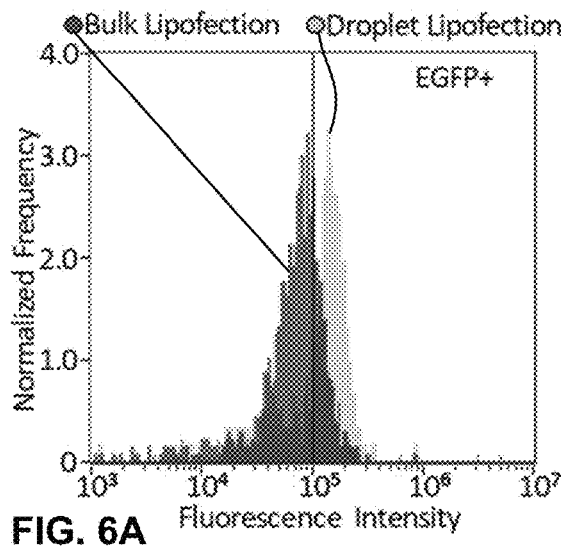
FIGS. 6A-6B show fluorescence intensity v.s. normalized cell-count frequency histograms (FIG. 6A) and the average EFGP transfection efficiencies (FIG. 6B) of HeLa cells transfected via droplet lipofection and conventional bulk lipofection.
Figure 6B:
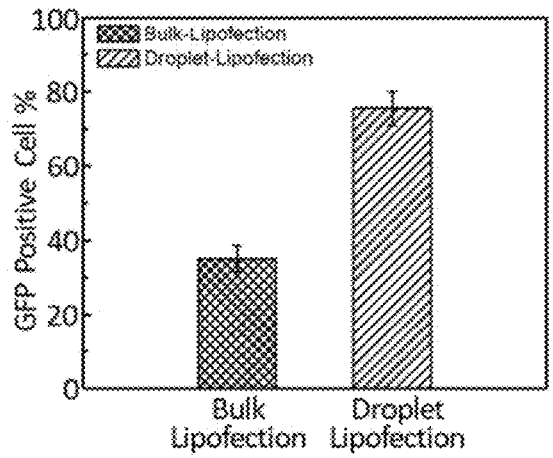

To compare the transfection efficiency between droplet microfluidics-based single-cell lipofection and conventional bulk lipofection, three types of suspension cells, i.e., K562, THP-1, and Jurkat, were transfected via both approaches and analyzed by flow cytometry 48 h after transfection with the pcDNA3-EGFP plasmid. As shown in the fluorescence intensity (x-axis) versus cell count (y-axis) plots of every 1,000 live transfected single cells for each cell lines (FIG. 3A), the droplet-lipofection histogram was significantly shifted towards a higher fluorescence intensity compared to the bulk-lipofection histogram, which demonstrated an overall higher EGFP expression level, and therefore a higher transfection efficiency for the droplet-lipofection group. The exact transfection efficiencies were calculated and compared in FIG. 3C. Using the platform, the transfection efficiency increased from 2.3±0.4% to 52.5±5.7% for Jurkat cells, from 3.8±0.5% to 46.3±5.4% for THP-1 cells, and from 4.8±0.9% to 51.8±3.3% for K562 cells. Referring to FIG. 3D, with respect to cell viability, the present platform realized a 10-fold increase in lipofection efficiency for hard-to-transfect suspension cells with a competitive cell viability as compared to the standard bulk approach. It has also demonstrated a better performance as compared to other non-viral methods that reported at most 32% transfection efficiency. As an examination of the platform's performance on adherent cells, which are easier to transfect compared to suspension cells, HeLa cells were also ran through the present droplet-lipofection device to transfect them with the same pcDNA3-EGFP plasmid, (FIG. 6A-6B). There was a clear increase in transfection efficiency when using droplet lipofection (75.5±4.6%) compared to using the conventional bulk lipofection protocol (35.1±3.6%), which supports that rapid cell-squeezing through droplet pinch-off together with chaotic mixing in the confined micro-droplet improved transfection efficiency.

Figure 3B:
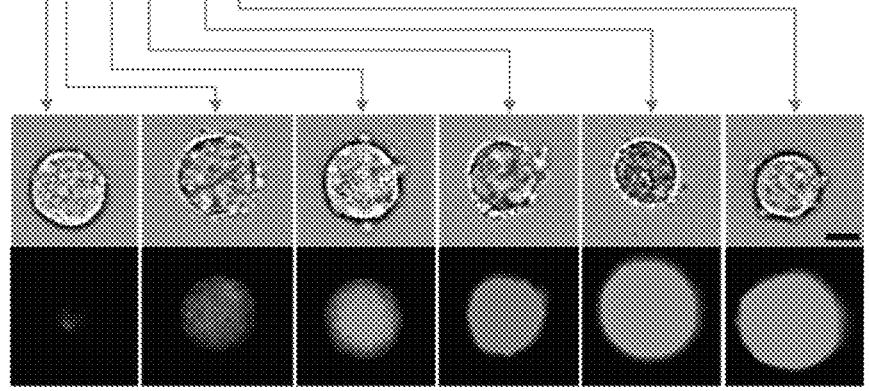
FIG. 3B displays bright-field (top) and fluorescent (bottom) images of single EGFP-transfected K562 cells at different fluorescence intensity values. The images were taken when individual cells passed through the detector in the ImageStream flow cytometer. Cells in the bulk lipofection group had various fluorescence intensities over a broad range, whereas cells in the droplet lipofection group had much smaller intensity variation. Scale bar: 7 μm.
Figure 3C:
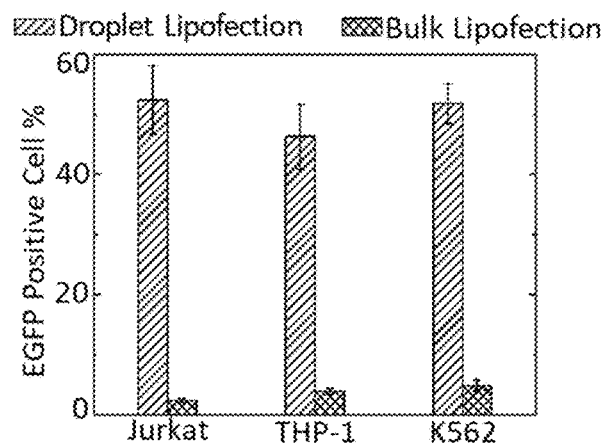
FIG. 3C shows an average transfection efficiency compared between the present droplet lipofection approach and the conventional bulk lipofection as measured by the percentage of EGFP-positive cells. Three repeat experiments were conducted for each cell line.
Figure 3D:
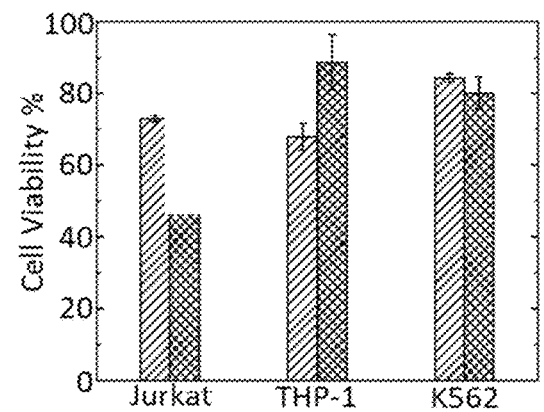
FIG. 3D shows cell viability compared between the present droplet lipofection approach and the conventional bulk lipofection as measured by the percentage of propodeum iodide-negative cells. Three repeat experiments were conducted for each cell line.
Figure 3E:
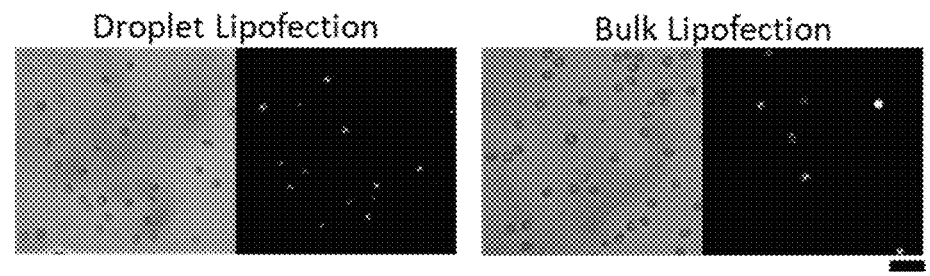
FIG. 3E displays bright-field and fluorescent images of K562 cells 48 hrs after transfection of pcDNA3-EGFP plasmid via droplet lipofection (left) and bulk lipofection (right). Scale bar: 100 μm.

Another significant result was that the histograms of the bulk transfected cells (FIG. 3A) had a broad distribution ranging from a very low fluorescence intensity to an extremely high intensity, which was also verified by the single-cell bright-field and fluorescent images taken when they passed through the flow cytometer (FIG. 3B). In contrast, cells transfected via droplet lipofection had a narrower fluorescence intensity distribution (FIG. 3A), and there were no super bright cells compared to the bulk method (FIG. 3E). Therefore, the present platform provided a much lower cell-to-cell transfection variability and a higher transfection consistency, which are important performance metrics in gene therapy. This transfection consistency was realized via droplet microfluidics and not in the bulk process, as the cell-encapsulating microdroplets generated on chip were monodisperse with a size deviation less than 2%, enabling quantitative and precise control of the reagents and manipulation applied to each individual cell. Benefiting from the chaotic advection and cell-squeezing through the droplet pinch-off, the present platform enabled ~10 times higher transfection efficiency than bulk and demonstrated a better performance as compared with other reported non-viral methods for suspension cell transfection.

CRISPR-Cas9 Gene Editing

Figure 4A:
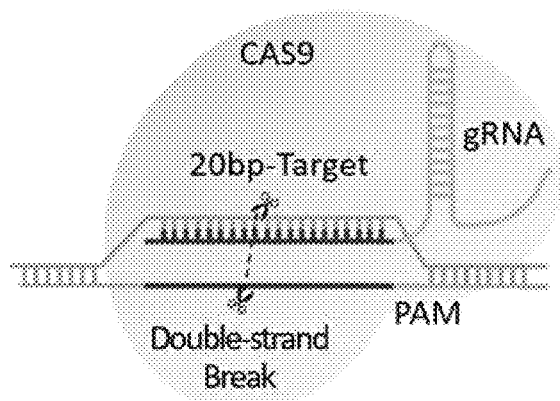
FIGS. 4A-4D shows targeted knockout of TP53BP1 in K562 cells through the delivery of pLentiCRISPR.v2-sgTP53BP1 plasmid via droplet lipofection.
Figure 4B:
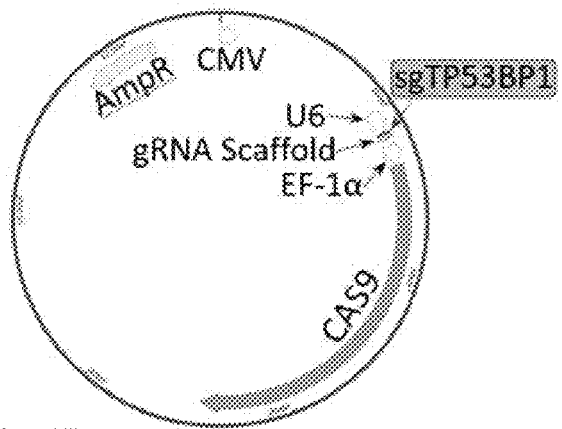
Figure 4C:
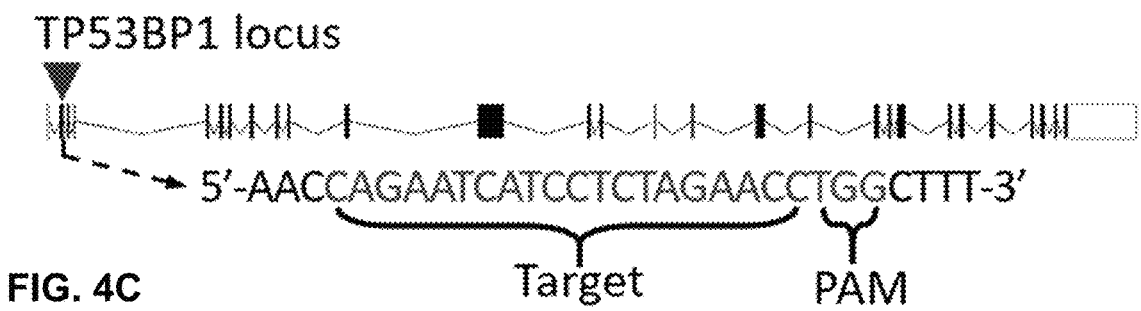
Figure 4D:
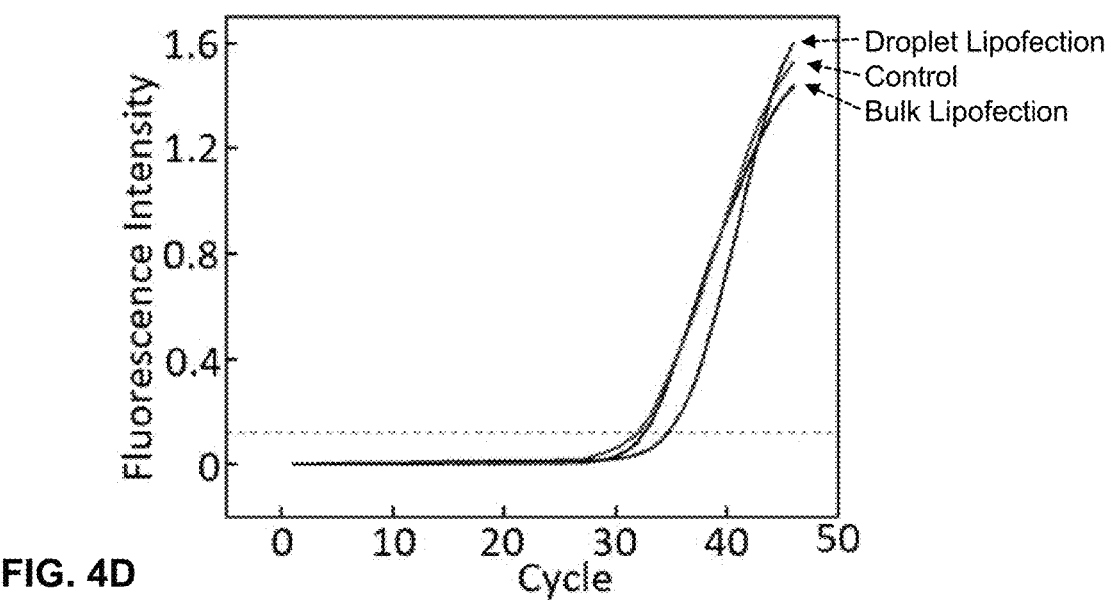
Figure 7A:
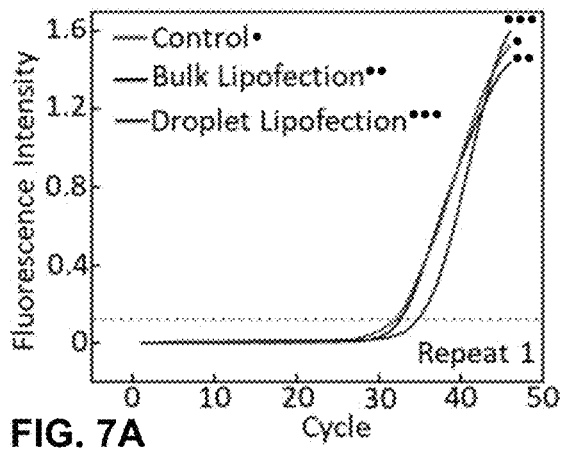
FIGS. 7A-7D show RT-qPCR results for analyzing the knockout efficiency of TP53BP1 in K562 cells via the CRISPR/CAS9 mechanism.
Figure 7B:
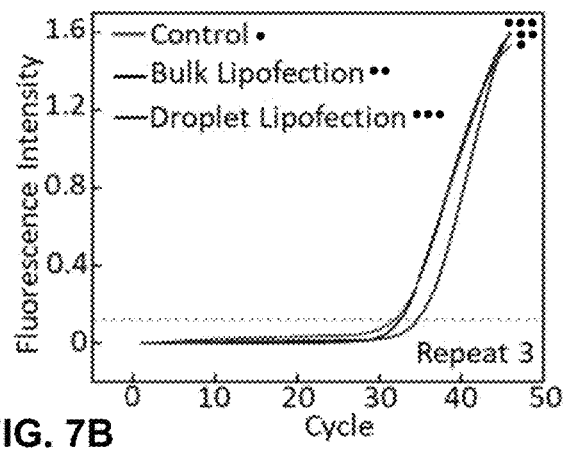
Figure 7C:
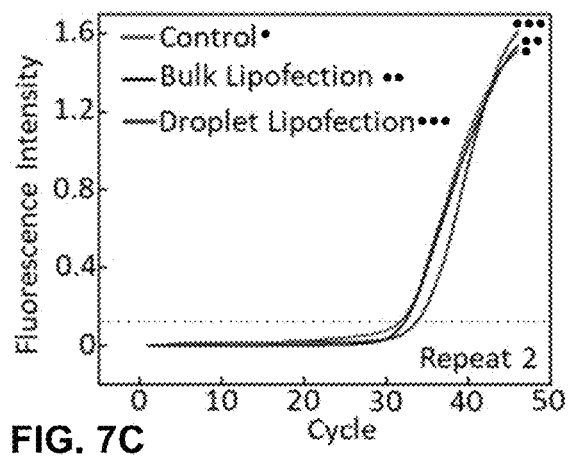

The platform of the present invention was implemented in CRISPR-CAS9-mediated targeted gene editing. The CRISPR-Cas9 system has been broadly used in biomedical research and clinical applications because of its high-efficiency and high-specificity in targeting the locus of interest. A 20-bp single-guide RNA (sgRNA) directs the Cas9 nuclease to introduce double-strand breaks at the sequence-specific genome locus, whereafter non-homologous end joining DNA-repairing mechanism is triggered, which generates gene mutation at the targeted locus (FIG. 4A). The mutation will often block the normal gene expression and results in gene knockout. As shown in FIG. 4C, a sgRNA sequence (SEQ ID NO: 1) targeting the 2nd exon of the TP53BP1 (tumor suppressor p53 binding protein 1) gene was designed and cloned in between a U6 promoter sequence and gRNA scaffold of the pLentiCRISPR v2 vector, which also carried the sequence of *S. pyogenes* CAS9 nuclease (FIG. 4B). The constructed plasmids were delivered into K562 cells via both droplet lipofection and the bulk method, and RT-qPCR of the targeted locus was performed for every 1,000 single cells 48 h after the initial delivery. As plotted in the representative RT-qPCR amplification curves (FIG. 4D) of three repeating experiments (FIGS. 7A-7C), the amplification curve of the bulk-lipofection group was very close to that of the non-transfected group, whereas the amplification curve of the droplet-lipofection group shifted towards a higher cycle-threshold (Ct) value, indicating a higher efficiency of gene knockout. The Ct value was 31.3±0.2 for the non-transfected group, 31.8±0.3 for the bulk-lipofection group, and 33.9±0.6 for the droplet-lipofection group.

Figure 7D:
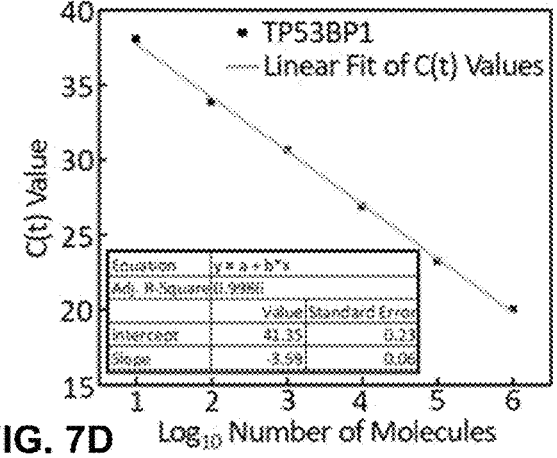

Upon calibration using the established standard curve (FIG. 7D), wherein the correlation between the absolute number of TP53BP1 mRNA molecules (n) and the Ct value was: $\text{Log}_{10}{}^n=(41.35-\text{Ct})/3.59$, the corresponding copy number of the target mRNA molecules was 630±61 for the non-transfected group, 457±83 for the bulk-lipofection group, and 119±51 for the droplet-lipofection group. Therefore, the estimated TP53BP1 knockout efficiency through the delivery of pLentiCRISPR.v2-sgTP53BP1 plasmid was 27±13% when using bulk lipofection, and 81±8% when using droplet lipofection. However, as the Cells-to-CT™ 1-Step Power SYBR Green Kit was used for this experiment, in which cell lysing, mRNA extraction and RT-qPCR were all integrated into one assay, there was an unavoidable loss of mRNA molecules during cell lysing and mRNA extraction, which caused an over-estimation of the gene knockout efficiency. Overall, the estimated knockout efficiency by droplet lipofection was satisfactory for this difficult-to-transfect lymphoma cell line that could not be achieved by current bulk lipofection methods.

Thus, based on the examples and results described herein, the present invention provides a droplet microfluidics-based single-cell transfection platform for lipoplex-mediated efficient and consistent plasmid delivery for hard-to-transfect suspension cells. In this platform, single cells were co-encapsulated with cationic lipids and plasmids in monodisperse micro-droplets, and chaotic mixing resulted in monodisperse lipoplexes for consistent and efficient transfection. Using the platform, the pcDNA3-EGFP plasmid delivery efficiency improved from ~5% to ~50% for all of the three tested suspension cell lines, i.e., K562, THP-1, Jurkat, with significantly reduced cell-to-cell variation, compared to the bulk method. The platform was also utilized in CRISPR/CAS9-mediated gene editing and demonstrated efficient targeted knockout of TP53BP1 gene in K562 cells. Without wishing to limit the present invention to a particular theory or mechanism, the platform had an order of magnitude higher transfection efficiency and much lower transfection variability (higher consistency) These features may be attributed to: 1) the chaotic mixing generating monodisperse lipoplexes in the proper size range for endocytosis, 2) confining a single-cell with lipoplexes in a picoliter-droplet plus chaotic advection to overcome the diffusion limitations in the bulk reaction volume while generating intensive lipoplex-cell collision, and 3) the membrane permeability increasing due to cell deformation resulting from the exerted shear stress as it passed through the droplet pinch-off orifice. Lipoplex-mediated single-cell transfection via droplet microfluidics can have broad applications in gene therapy and regenerative medicine by providing higher transfection efficiency and lower cell-to-cell variation for hard-to-transfect cells, such as lymphoma and hematopoietic cells.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Reference numbers recited in the claims below are exemplary and solely for ease of review and examination of this patent application by the patent office only, and are not limiting in any way. The reference numbers are not intended in any way to limit the scope of the claims to the particular features having the corresponding reference numbers in the drawings. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of transfecting a cell (101), said method comprising:
   a. providing a microfluidic system (100), said system (100) comprising a microfluidic device (110) comprising:
      i. a first aqueous phase channel (115a);
      ii. a second aqueous phase channel (115b);
      iii. a combining channel (118) having an inlet end and a shearing outlet end, wherein the first aqueous phase channel (115a) and the second aqueous phase channel (115b) are fluidly connected to the inlet end of the combining channel;
      iv. a continuous phase channel network (116) comprising a first continuous phase channel (117a) and a second continuous phase channel (117b), wherein an outlet end of each continuous phase channel is fluidly connected to the shearing outlet end of the combining channel thus forming a droplet shearing junction (205) having a constricting droplet pinch-off orifice; and
      v. a rendering channel (120) having an inlet end fluidly connected to the droplet shearing junction (205), wherein at least a section of the rendering channel comprises a winding serpentine channel (125);
   b. introducing a first aqueous solution and the second aqueous solution into their respective aqueous phase channels (115a, 115b), wherein the first aqueous solution comprises cells (101) and transfection molecules (101), wherein the second aqueous solution comprises transfection reagents (103);
   c. combining the first and second aqueous solutions at the combining channel (118);
   d. introducing a continuous phase fluid into the continuous phase channels (117a, 117b);
   e. combining the continuous phase fluids with the combined aqueous solutions at the droplet shearing junction (205);
   f. shearing the combined aqueous solutions to form droplets (210) at the constricting droplet pinch-off orifice, wherein at least one cell (101), at least one transfection molecule (102), and at least one transfection reagent (103) are encapsulated in one droplet (210), wherein a flow rate of the combined aqueous solutions and a flow rate of the continuous phase fluids are adjusted such that the droplets (210) are formed in a dripping regime, wherein a ratio of the flow rate of the continuous phase fluids to the flow rate of the combined aqueous solutions is at least 5, wherein a capillary number (Ca) of the dripping regime is Ca>0.1,
   wherein in the dripping regime, the constricting droplet pinch-off orifice squeezes and exerts shear stress on the at least one cell (101) as it passes through the constricting droplet pinch-off orifice, thereby increasing membrane permeability due to cell deformation; and
   g. flowing the droplets (210) through the rendering channel (120), wherein flow of the droplets through the winding serpentine channel (125) induces chaotic advection that causes the transfection molecules (102) and transfection reagents (103) to form lipoplexes, and applies shear stress to the cells (101), thereby increasing membrane permeability to allow for transport of the lipoplexes through the cell membrane, thus transfecting the cells (101).

2. The method of claim 1, wherein the shearing outlet end is tapered.

3. The method of claim 1, wherein the first continuous phase channel (117a) and the second continuous phase channel (117b) are disposed on opposite sides of the combining channel (118).

4. The method of claim 1, wherein a section of the first continuous phase channel connected to the shearing outlet end and a section of the second continuous phase channel connected to the shearing outlet end are orthogonal to the combining channel (118).

5. The method of claim 1, wherein the rendering channel (120) is fluidly connected to the outlet ends of the continuous phase channels.

6. The method of claim 1, wherein the inlet end of the rendering channel has an arrowhead shape such that the inlet end tapers at the droplet shearing junction (205), gradually widens, and then narrows as it transitions to a straight portion of the rendering channel.

7. The method of claim 1, wherein the continuous phase fluid comprises an oil.

8. The method of claim 1, wherein the transfection reagents (103) comprise cationic lipids, helper lipids, or a combination thereof.

9. The method of claim 1, wherein the transfection molecules (102) comprise DNA, RNA, protein, a carbohydrate, a small molecule, or a combination thereof.

10. The method of claim 1, wherein the transfection molecules (102) comprise CRISPR-CAS transfection molecules.

11. The method of claim 10, wherein the CRISPR-CAS transfection molecules are DNA vectors encoding single guide RNA (sgRNA), DNA vectors encoding CAS nuclease gene, DNA vectors encoding both sgRNA and CAS nuclease gene, sgRNA or other RNA molecules, CAS nuclease or other protein molecules, sgRNA-CAS complexes, or other DNA or RNA and protein complexes.

12. The method of claim 10, wherein the CRISPR-CAS transfection molecules modify a gene by utilizing a targeting sequence complementary to a target DNA sequence in the gene, wherein when the targeting sequence interacts with the target DNA sequence, a CAS nuclease is guided to the target sequence and cleaves the target DNA at the target sequence to produce double strand breaks, which are then repaired by the cell, thus leading to modification of the gene.

13. The method of claim 12, wherein said modification of the gene is addition, deletion, replacement, or mutation.

14. The method of claim 1, wherein the cells (101) are eukaryotic cells, prokaryotic cells, or a combination thereof.

15. The method of claim 14, wherein the prokaryotic cells are bacterial cells.

16. The method of claim 14, wherein the eukaryotic cells are animal cells, plant cells, algae cells, fungal cells, or a combination thereof.

17. The method of claim 1, wherein the cells (101) are protoplasts, pollen grains, microspores, tetrads, or a combination thereof.

18. The method of claim 1, wherein fluid flow in the device is pressure-driven.

* * * * *